(12) United States Patent
Kamatani et al.

(10) Patent No.: US 8,968,890 B2
(45) Date of Patent: Mar. 3, 2015

(54) ORGANIC COMPOUND AND ORGANIC LIGHT-EMITTING DEVICE HAVING THE SAME

(75) Inventors: Jun Kamatani, Tokyo (JP); Naoki Yamada, Inagi (JP); Kengo Kishino, Tokyo (JP); Masanori Muratsubaki, Hachioji (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 345 days.

(21) Appl. No.: 13/634,701

(22) PCT Filed: Jun. 7, 2011

(86) PCT No.: PCT/JP2011/063442
§ 371 (c)(1),
(2), (4) Date: Sep. 13, 2012

(87) PCT Pub. No.: WO2011/158767
PCT Pub. Date: Dec. 22, 2011

(65) Prior Publication Data
US 2013/0001543 A1    Jan. 3, 2013

(30) Foreign Application Priority Data

Jun. 18, 2010    (JP) .................................. 2010-139959

(51) Int. Cl.
| | | |
|---|---|---|
| H01L 51/54 | (2006.01) |
| H01L 27/32 | (2006.01) |
| H01L 51/00 | (2006.01) |
| C07C 13/62 | (2006.01) |
| C09K 11/06 | (2006.01) |
| H01L 51/50 | (2006.01) |

(52) U.S. Cl.
CPC ............ *H01L 51/0056* (2013.01); *C07C 13/62* (2013.01); *C09K 11/06* (2013.01); *C07C 2103/54* (2013.01); *C09K 2211/1007* (2013.01); *C09K 2211/1011* (2013.01); *C09K 2211/1029* (2013.01); *H01L 51/5012* (2013.01); *Y10S 428/917* (2013.01)
USPC ........... 428/690; 428/917; 313/504; 313/506; 257/40

(58) Field of Classification Search
None
See application file for complete search history.

(56) References Cited

U.S. PATENT DOCUMENTS

2002/0168544 A1*  11/2002  Fukuoka et al. .............. 428/690

FOREIGN PATENT DOCUMENTS

| JP | 2005302667 A | 10/2005 |
| JP | 2007142171 A | 6/2007 |
| JP | 2009152529 A | 7/2009 |
| JP | 2009302470 A | 12/2009 |
| JP | 2010143880 A | 7/2010 |
| JP | 2011168504 A | 9/2011 |
| WO | 01023497 A1 | 4/2001 |

* cited by examiner

*Primary Examiner* — Dawn L. Garrett
(74) *Attorney, Agent, or Firm* — Canon U.S.A., Inc. IP Division

(57) ABSTRACT

Provided are a novel organic compound suitable for emitting green light and an organic light-emitting device including the compound. The organic compound is that shown in claim 1. The organic compound shown in claim 1 has substituents that are each independently selected from the group consisting of hydrogen atoms, halogen atoms, optionally substituted alkyl groups, optionally substituted alkoxy groups, substituted amino groups, optionally substituted aryl groups, and optionally substituted heterocyclic groups.

7 Claims, 1 Drawing Sheet

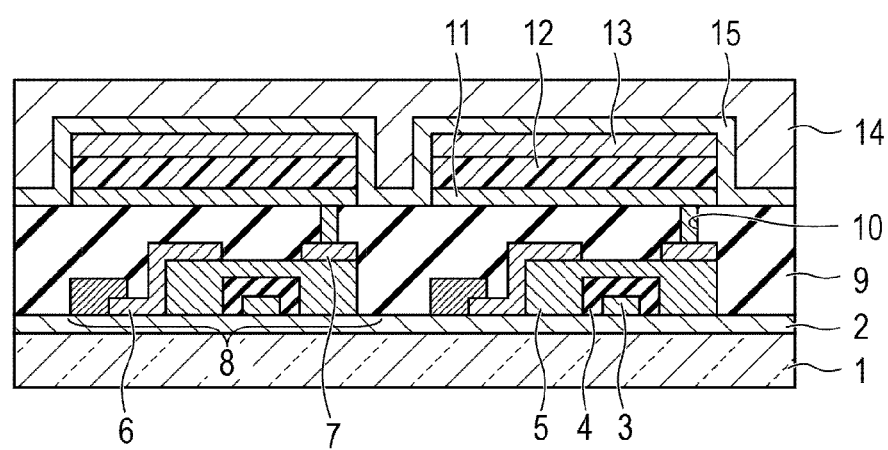

ORGANIC COMPOUND AND ORGANIC LIGHT-EMITTING DEVICE HAVING THE SAME

TECHNICAL FIELD

The present invention relates to a novel organic compound and an organic light-emitting device having the same.

BACKGROUND ART

An organic light-emitting device includes an organic compound layer between a pair of electrodes and generates excitons of the organic compound by injecting electrons or holes (electron holes) from each electrode to the organic compound layer and utilizes the light emitted when the excitons return to the ground state. The organic light-emitting device is also called an organic electroluminescence (EL) device. It is important to create novel compounds for providing high-performance organic light-emitting devices, and novel compounds have been actively developed up to now. For example, Patent Literature 1 describes a compound that emits green light as an example of a material that is used for the light-emitting layer of an organic light-emitting device.

CITATION LIST

Patent Literature

PTL 1 Japanese Patent Laid-Open No. 2005-302667

SUMMARY OF INVENTION

The organic compound described in PTL 1 cannot emit green light with its basic skeleton only. It is known that the light emission wavelength of a light-emitting material can be adjusted by introducing a substituent, but it may deteriorate the stability of the compound.

Accordingly, the present invention provides a novel organic light-emitting device having organic compound that can emit light in a green color region by its basic skeleton only.

According to the present invention, provided is an organic light-emitting device including a cathode, an anode, and organic compound layers disposed between the anode and the cathode, wherein at least one layer of the organic compound layers contains the organic compound represented by the following Formula (1):

[Chem. 1]

(1)

In Formula (1), $R_1$ to $R_{18}$ are each independently selected from the group consisting of hydrogen atoms, halogen atoms, optionally substituted alkyl groups, optionally substituted alkoxy groups, substituted amino groups, optionally substituted aryl groups, and optionally substituted heterocyclic groups.

According to the present invention, a novel organic compound having a broad band gap by the basic skeleton itself and a deep lowest unoccupied molecular orbital (LUMO) level can be provided. The organic compound according to the present invention can emit light in a green color region by the basic skeleton itself. In addition, it is possible to provide a novel organic compound that can emit not only green light but also red light by introducing a substituent into the basic skeleton. Furthermore, organic light-emitting devices having these novel organic compounds can be provided.

BRIEF DESCRIPTION OF DRAWINGS

FIG. 1 is a schematic cross-sectional view illustrating organic light-emitting devices and switching devices connected to the organic light-emitting devices.

DESCRIPTION OF EMBODIMENTS

The novel organic light-emitting device according to the present invention has an organic compound represented by the following Formula (1):

[Chem. 2]

In Formula (1), $R_1$ to $R_{18}$ are each independently selected from the group consisting of hydrogen atoms, halogen atoms, optionally substituted alkyl groups, optionally substituted alkoxy groups, substituted amino groups, optionally substituted aryl groups, and optionally substituted heterocyclic groups.

Herein, in Formula (1), examples of the alkyl group include a methyl group, an ethyl group, a n-propyl group, an isopropyl group, a n-butyl group, an isobutyl group, a sec-butyl group, a tert-butyl group, an octyl group, a 1-adamantyl group, and a 2-adamantyl group, but are not limited thereto.

Herein, in Formula (1), examples of the alkoxy group include a methoxy group, an ethoxy group, a propoxy group, a 2-ethyl-octyloxy group, a phenoxy group, a 4-tert-butylphenoxy group, a benzyoxy group, and a thienyloxy group, but are not limited thereto.

Herein, in Formula (1), examples of the amino group include an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-methyl-N-phenylamino group, an N,N-dimethylamino group, an N-phenyl-N-(4-tert-butylphenyl)amino group, and an N-phenyl-N-(4-trifluoromethylphenyl)amino group, but are not limited thereto.

Herein, in Formula (1), examples of the aryl group include a phenyl group, a naphthyl group, an indenyl group, a biphenyl group, a terphenyl group, and a fluorenyl group, but are not limited thereto.

Herein, in Formula (1), examples of the heterocyclic group include a pyridyl group, an oxazolyl group, an oxadiazolyl group, a thiazolyl group, a thiadiazolyl group, a carbazolyl group, an acridinyl group, and a phenanthrolyl group, but are not limited thereto.

In Formula (1), examples of the substituent of the amino group include alkyl groups such as a methyl group, an ethyl group, and a propyl group; aryl groups such as a phenyl group and a biphenyl group; and heterocyclic groups such as a pyridyl group and a carbazolyl group.

In Formula (1), the aryl group and the heterocyclic group may each have an alkyl group having 1 to 4 carbon atoms.

The present inventors have paid attention to a basic skeleton itself. Specifically, the inventors have tried to provide a compound having a basic molecular skeleton that emits by itself light having a wavelength within a desired light emission wavelength region.

In the present invention, the term "basic skeleton" refers to a structure that is constituted of only fused ring structures with conjugation.

In order to obtain a desired light emission wavelength, it is known to induce a substituent to the basic skeleton, but in such a case, the stability of the compound may be deteriorated.

The organic compound according to the present invention emits light in a green color region by only the basic skeleton. Specifically, the green color region is from 480 to 530 nm.

The luminous efficiency of an organic light-emitting device can be increased by using a light-emitting material having a high quantum yield. This is achieved by, (1) a high oscillator strength, or
(2) a small oscillation portion of the skeleton involving in light emission.

Furthermore, it is important that a material suitable for emitting green light as an organic light-emitting device has an emission peak in the range of from 480 to 530 nm when the light-emitting material is in a solution state.

In order to achieve the above-mentioned requirement (1), it is important to enhance the symmetry of the skeleton involving in the light emission of the light-emitting material. This is because a molecule having high symmetry can easily align the orientation of transition dipole moments of atoms to give a large transition dipole moment. A larger transition dipole moment leads to higher oscillation strength, resulting in a high quantum yield.

Furthermore, extension in conjugation in one direction leads to an increase in transition dipole moment of a molecule, resulting in an increase in oscillation strength.

From this point, the organic compound according to the present invention has a fused ring structure in which the conjugation extends in a position from the 9-position to the 10-position of a benzo[k]fluoranthene. This structure provides a larger transition dipole moment compared to that of the benzo[k]fluoranthene. Therefore, the organic compound according to the present invention has a structure having high oscillation strength.

As for the above-mentioned requirement (2), a structure not having a rotational structure in its skeleton involving in light emission inhibits energy provided to the organic compound from being converted into kinetic energy such as rotation or oscillation. Therefore, the ratio of energy emitted as photons can be increased. That is, a decrease in quantum yield can be inhibited. Comparison of organic compound according to the present invention with another organic compound An organic compound of the present invention is compared with a benzo[k]fluoranthene derivative as a compound similar to the compound of the present invention. 7,12-Diphenylbenzo[k]fluoranthene, which is a benzo[k]fluoranthene derivative having phenyl groups at the 7-position and the 12-position, and an organic compound (example compound A2) of the present invention are compared to confirm that the maximum light emission wavelength of the compound of the present invention is about 490 nm to emit light in a green color region, whereas that of the benzo[k]fluoranthene derivative is 428 nm.

[Chem. 3]

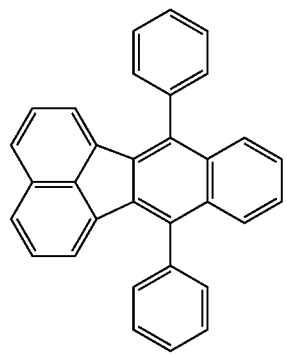

7,12-Diphenylbenzo[k]fluoranthene

[Chem. 4]

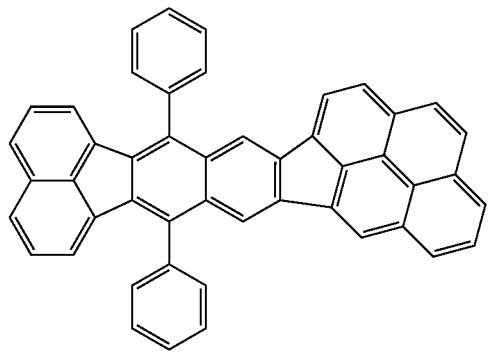

Example compound A2

From the above, it is confirmed that the compound of the present invention emits light suitable for green light emission by the basic skeleton only and provides a high quantum yield.

In addition, since the organic compound according to the present invention has two five-membered ring structures in its skeleton, the highest occupied molecular orbital (HOMO) energy level and the lowest unoccupied molecular orbital (LUMO) energy level are low. A low oxidation potential leads to an increase in energy necessary for oxidation, resulting in high stability against oxidation. Furthermore, the compound can be a suitable electron-trap type light-emitting material as a guest material of a light-emitting layer.

The organic compound according to the present invention does not have hetero atoms such as nitrogen atoms in the basic skeleton. This also contributes to the low oxidation potential, that is, contributes to the high stability against oxidation of the organic compound.

The organic compound according to the present invention can be used as a guest material of the light-emitting layer of an organic light-emitting device, in particularly, as a guest material of a green light-emitting device.

The organic compound according to the present invention can be converted into a red light-emitting material by providing to the basic skeleton of the compound a substituent that shifts the light emission wavelength to a longer wavelength. Since this resulting material having a longer light emission wavelength has the same basic skeleton as that of the organic compound according to the present invention, the material is stable against oxidation.

Examples of the substituent that shifts the light emission wavelength to a longer wavelength include aryl groups and triarylamino groups.

The positions of substitution for efficiently shifting the light emission wavelength to a longer wavelength are $R_1$, $R_2$, $R_3$, $R_8$, $R_9$, $R_{10}$, $R_{11}$, $R_{12}$, $R_{13}$, and $R_{18}$.

The light-emitting layer can contain a guest material of the organic compound according to the present invention and a host material having a LUMO higher than that of the organic compound, in other words, a material having a LUMO closer to a vacuum level. This is because that the organic compound according to the present invention has a low LUMO level and can therefore satisfactorily receive electrons supplied to the light-emitting layer, that is, the host material.

The organic compound according to the present invention may be used not only in the light-emitting layer but also in any layer, that is, a hole-injecting layer, a hole-transporting layer, a hole/exciton blocking layer, an electron-transporting layer, or an electron-injecting layer.

The organic compound according to the present invention has a broad band gap of the basic skeleton itself and, therefore, can be also used as a host material of a yellow or red light-emitting layer.

Herein, the term "host material" refers to a material having a largest weight ratio among the compounds constituting a light-emitting layer, and the term "guest material" refers to a material having a weight ratio smaller than that of the host material among the compounds constituting a light-emitting layer and performs main light emission. The term "assist material" refers to a material having a weight ratio smaller than that of the host material among the compounds constituting a light-emitting layer and mainly assists the light emission of the guest material. Examples of organic compound according to the present invention Specific examples of the organic compound according to the present invention will be shown below, but the present invention is not limited thereto.

[Chem. 5]

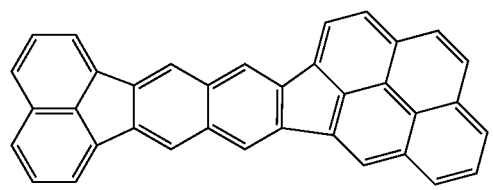

A1

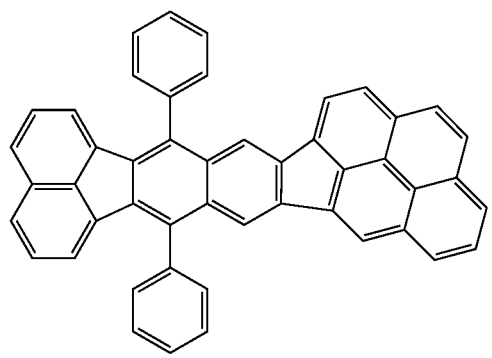

A2

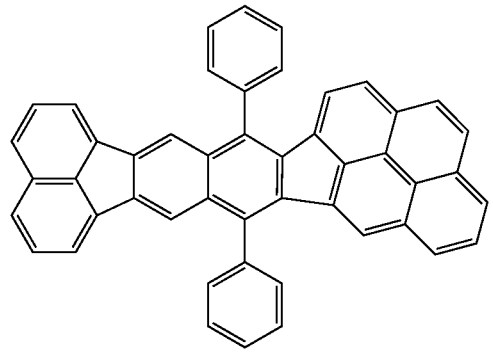

A3

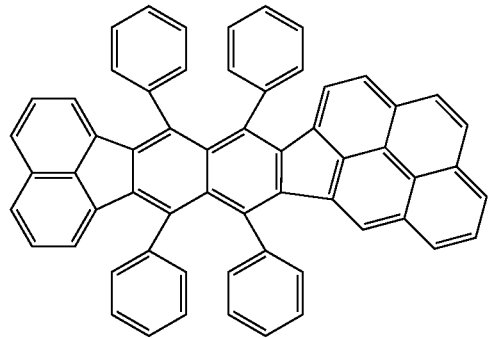

A4

-continued
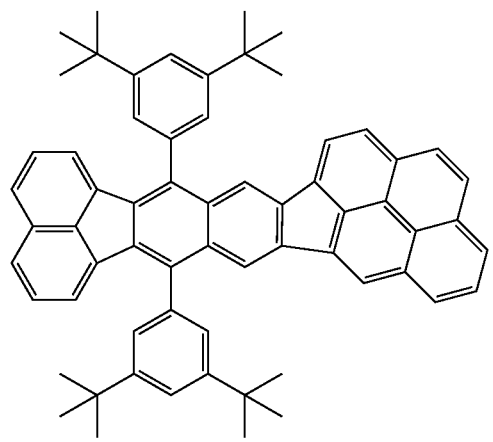
A5
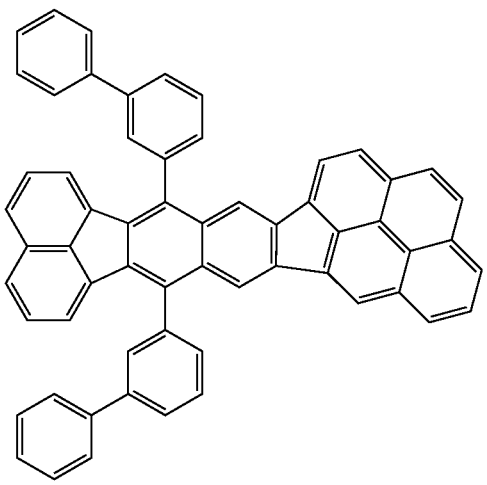
A6
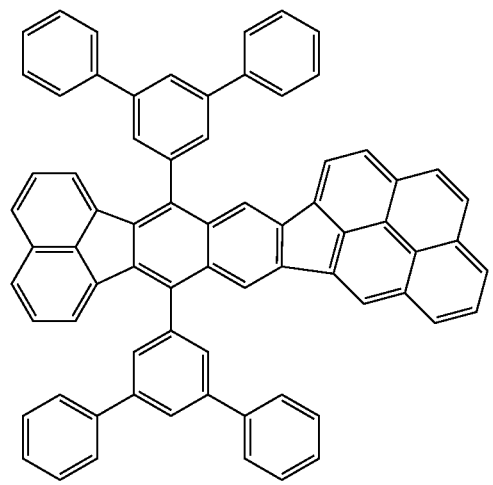
A7
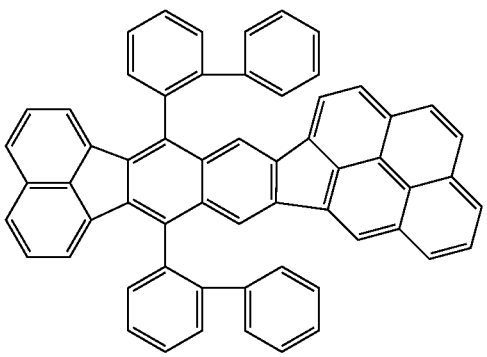
A8
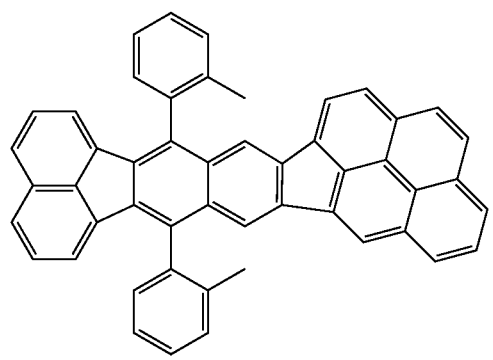
A9
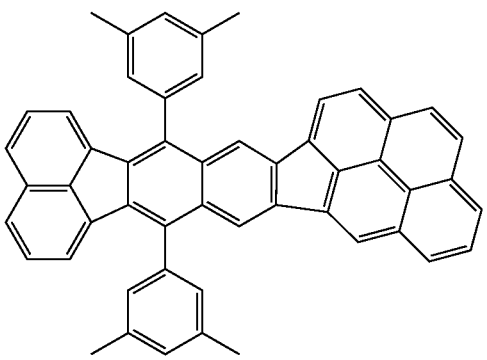
A10

-continued
A11
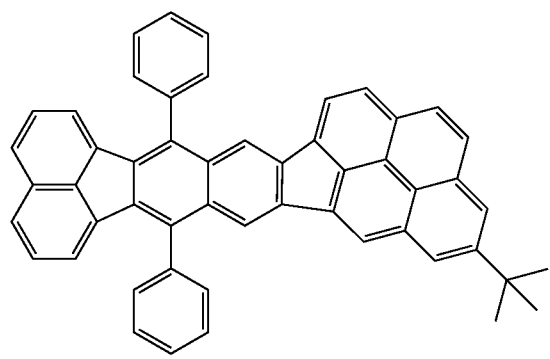
A12
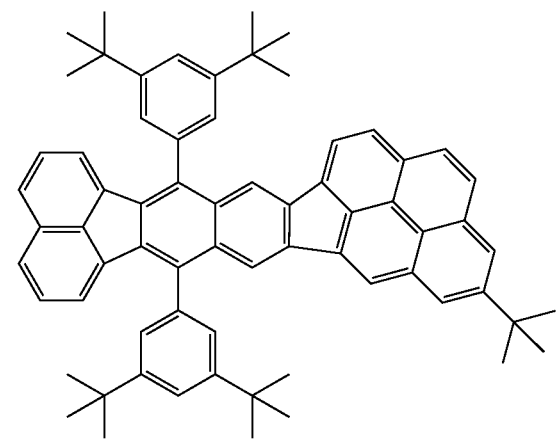
A13
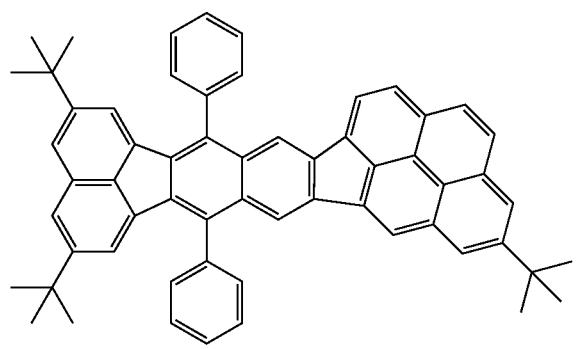
A14
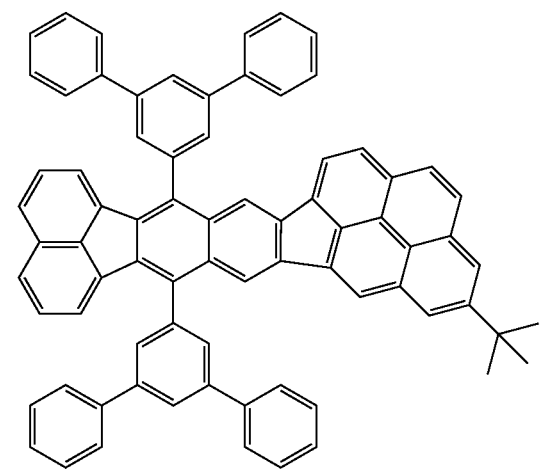
A15
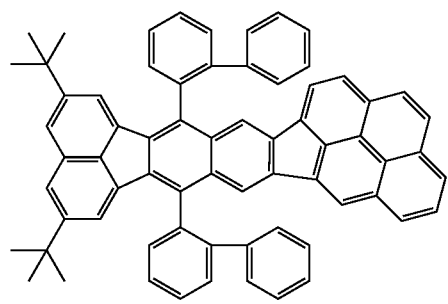
A16
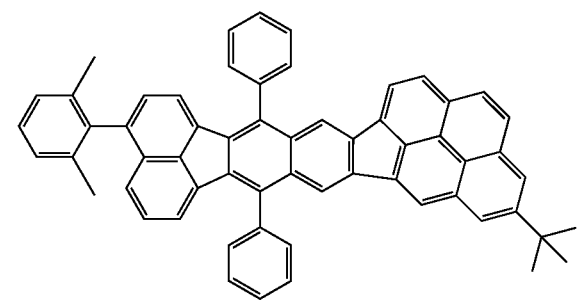

-continued
A17
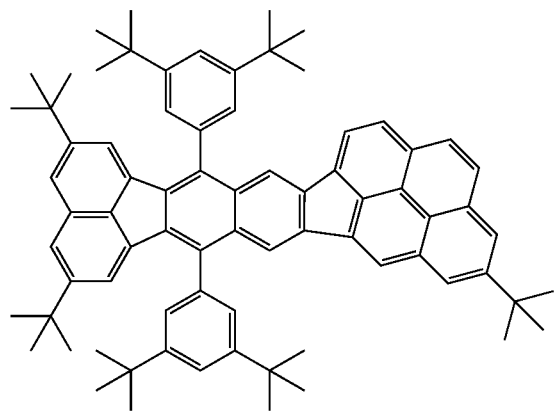
A18
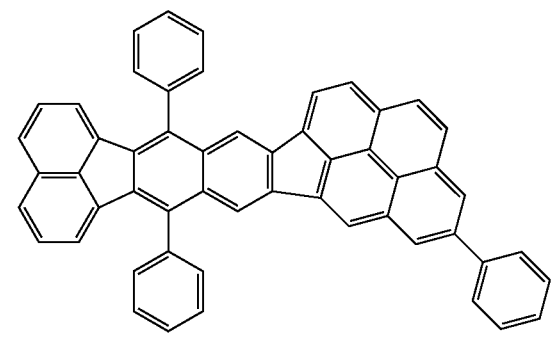
A19
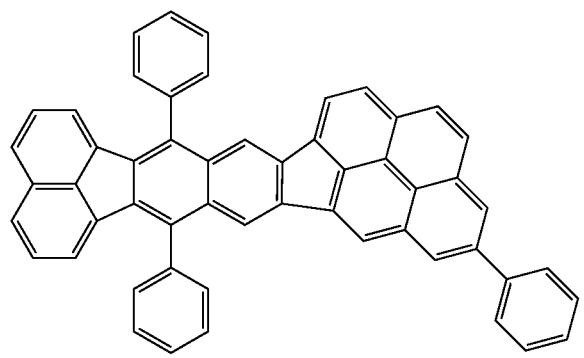
A20
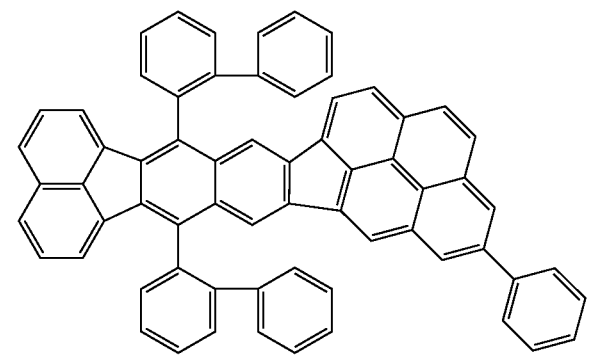
A21
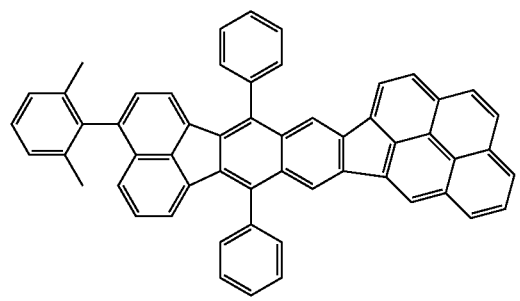
A22
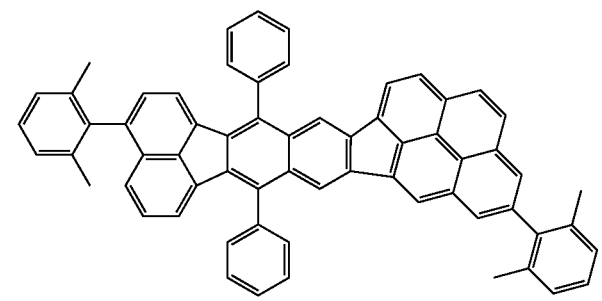
A23
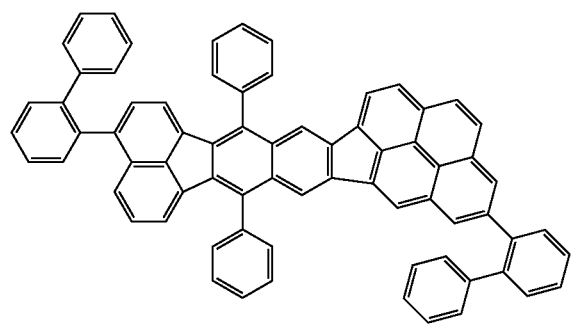
A24
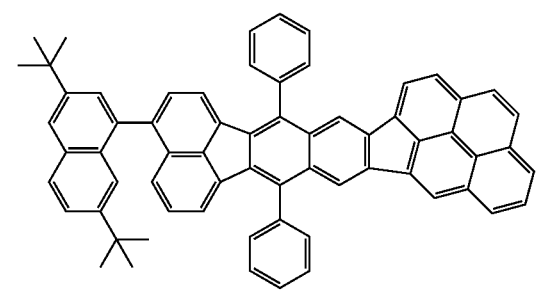

[Chem. 6]
A25
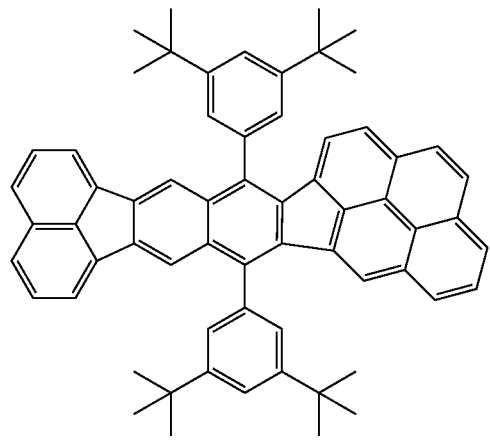
A26
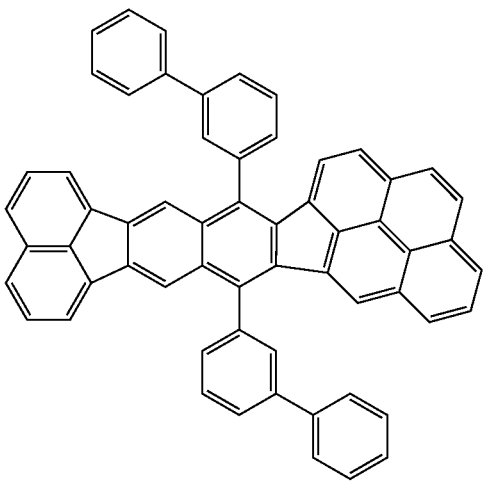
A27
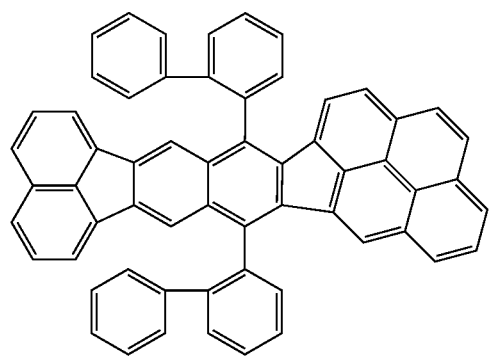
A28
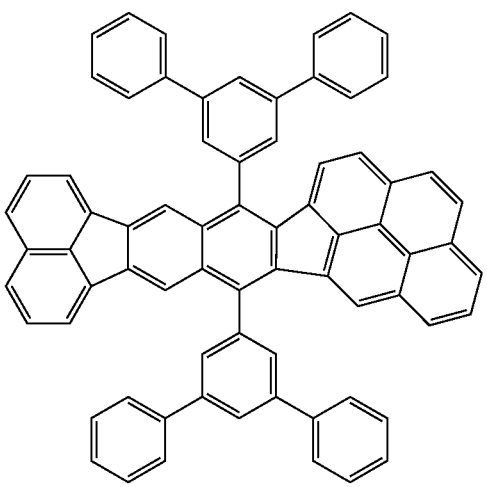
A29
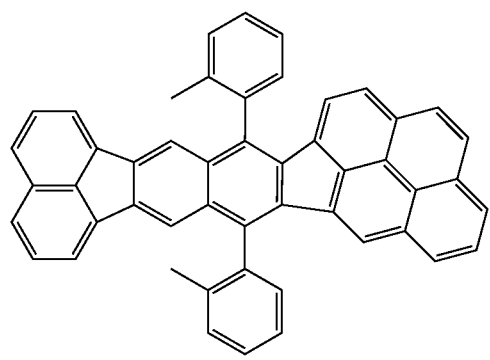
A30
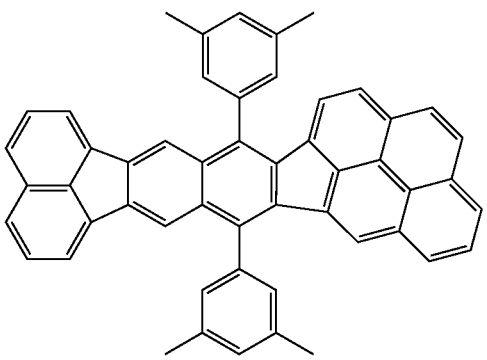

-continued
A31
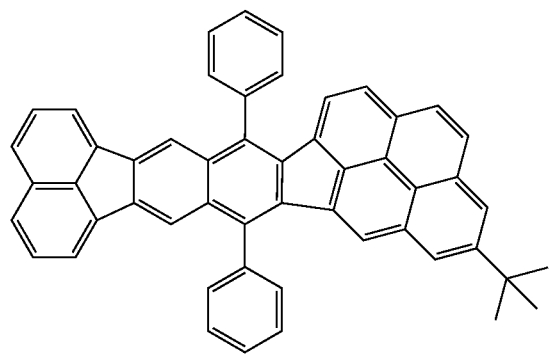
A32
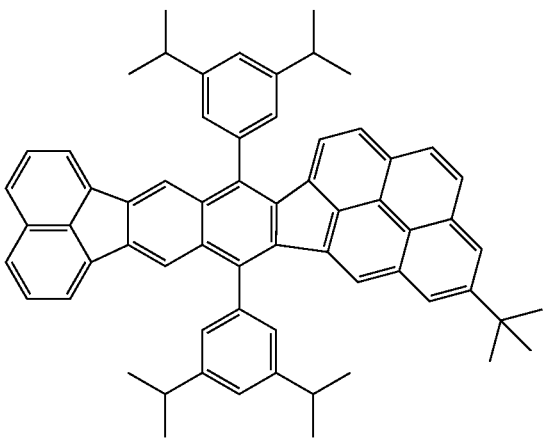
A33
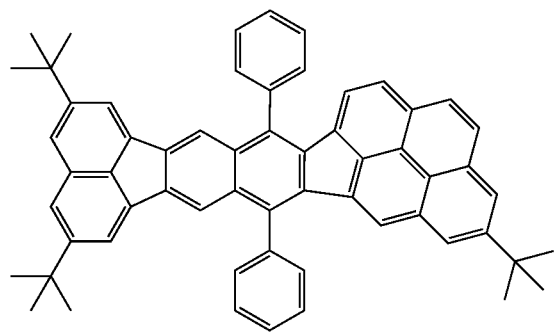
A34
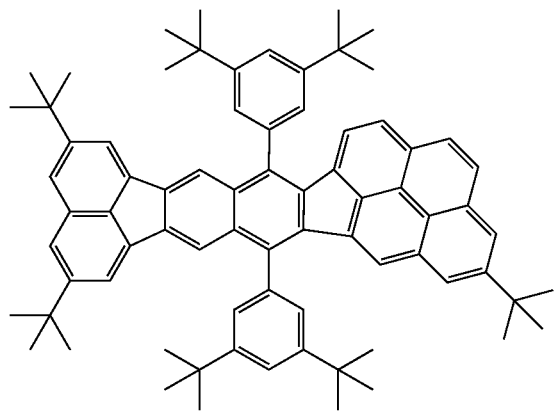
A35
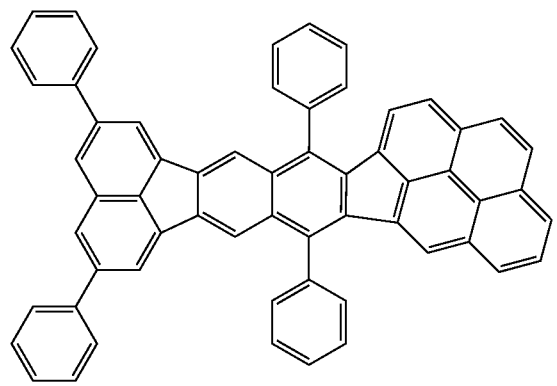
A36
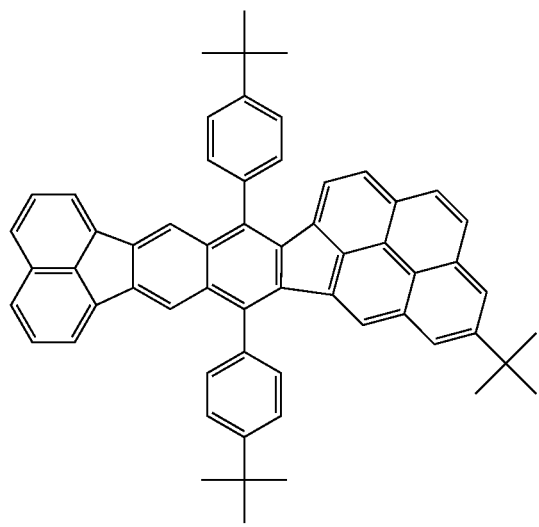

-continued
A37
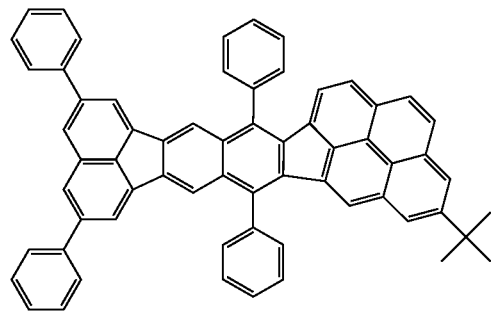
A38
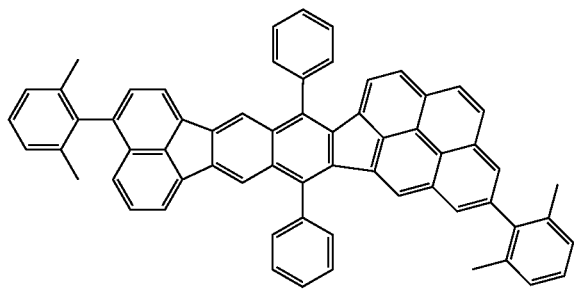
A39
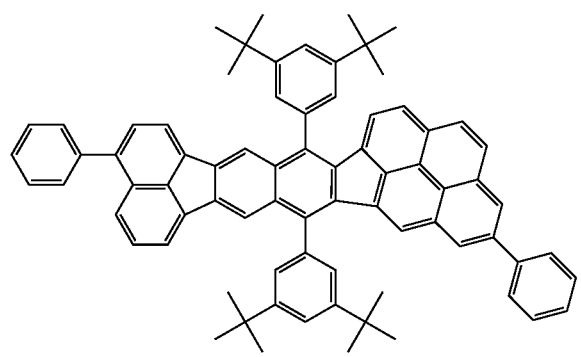
A40
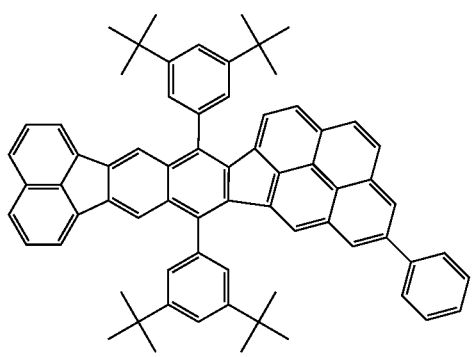
A41
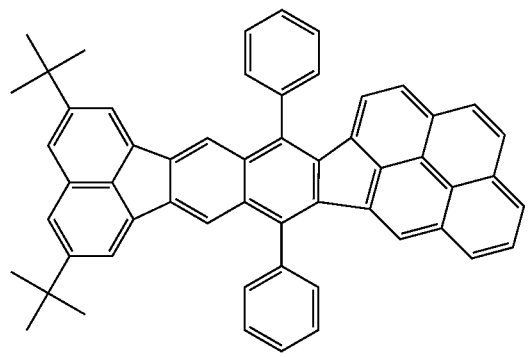
A42
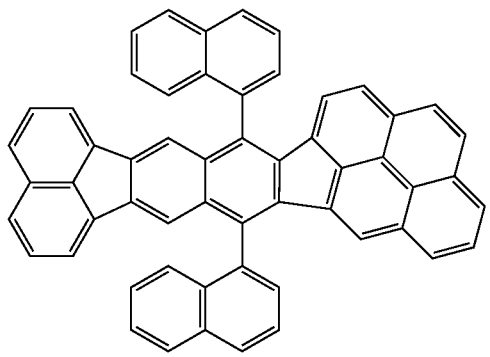
A43
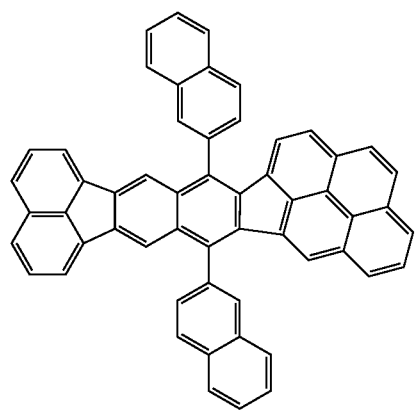
A44
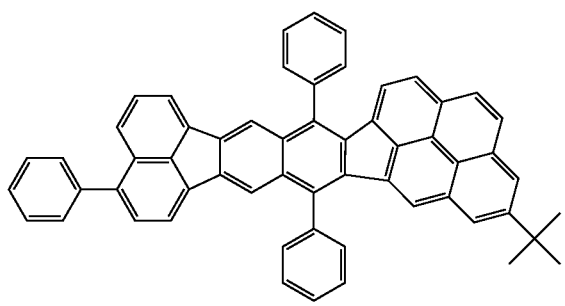

-continued
A45
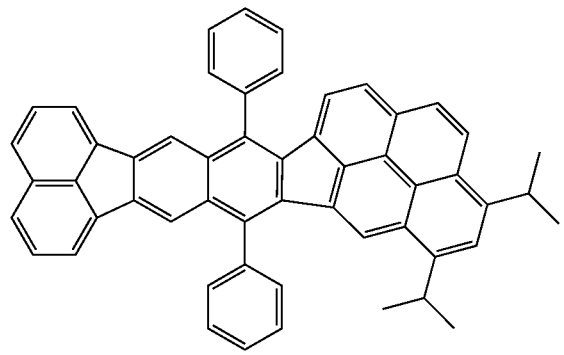
A46
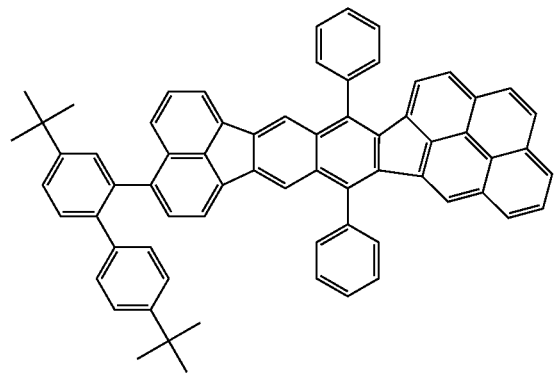
A47
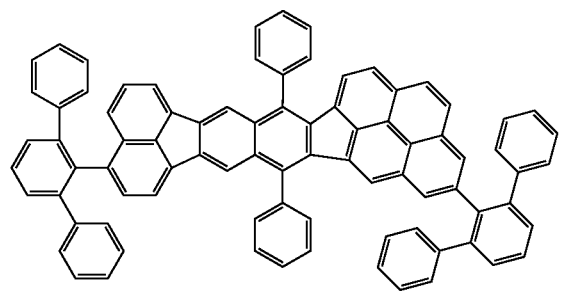
A48
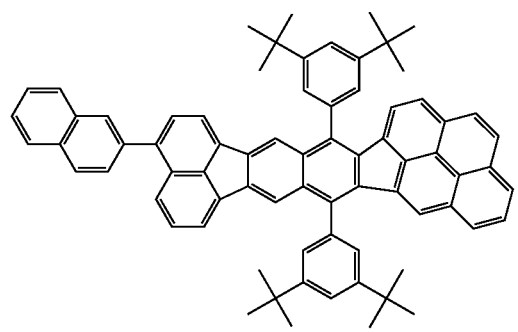
[Chem. 7]
B1
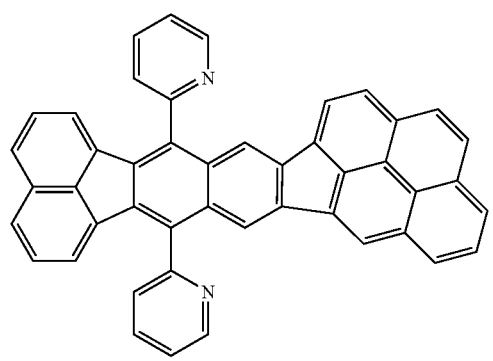
B2
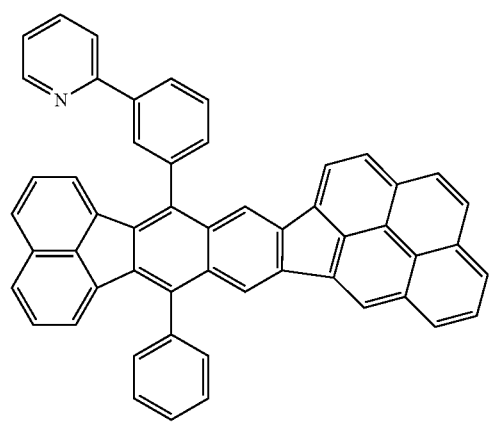

-continued
B3
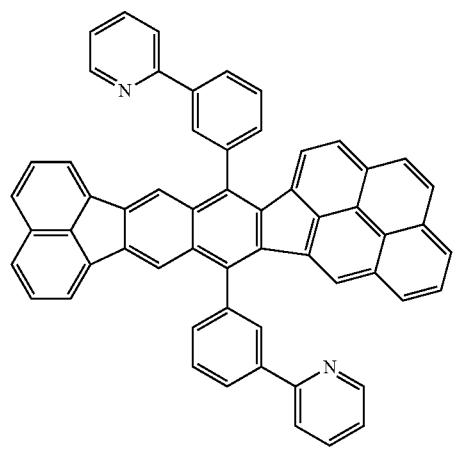
B4
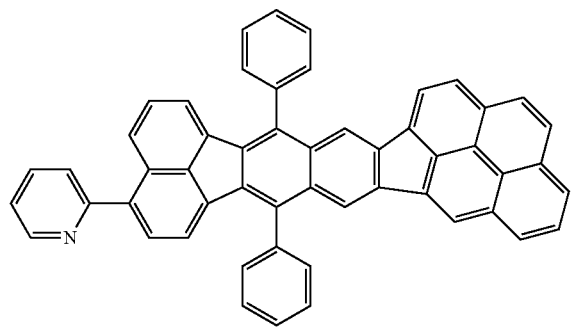
B5
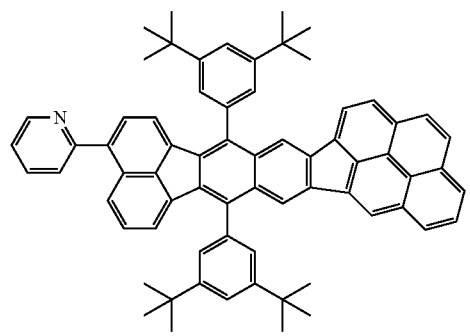
B6
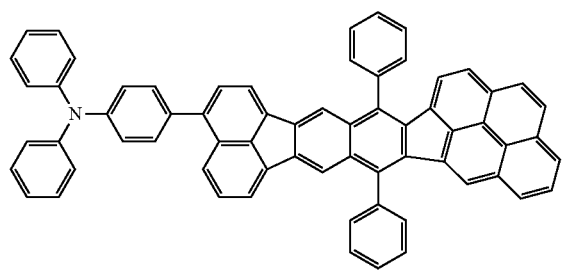
B7
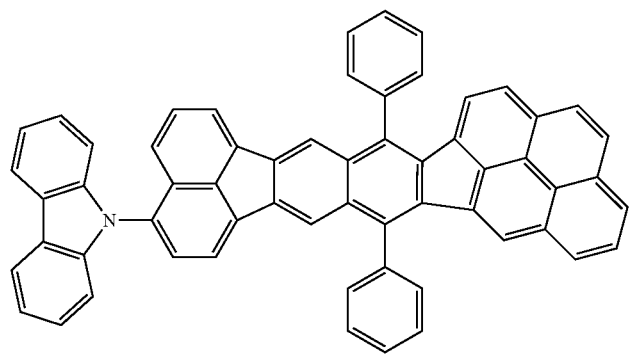
B8
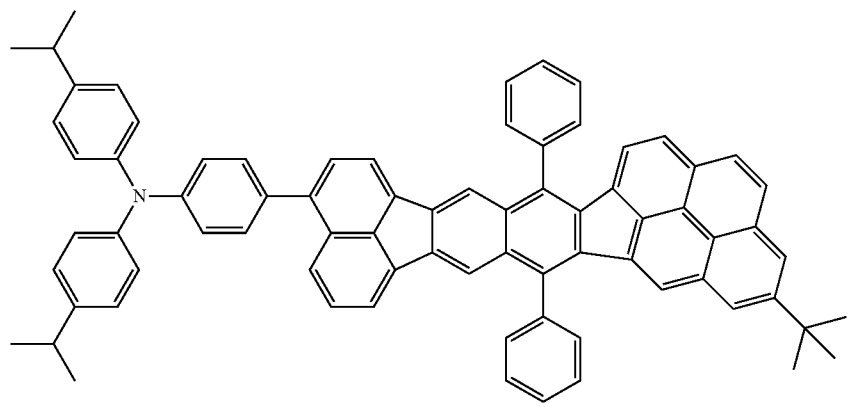

Characteristics of each Exemplified Compound Group

The compounds belonging to group A are each composed of only hydrocarbons over the entire molecule. Compounds composed of only hydrocarbons have low HOMO energy levels. Therefore, the oxidation potentials thereof are low, that is, such organic compounds are stable against oxidation.

Accordingly, among the organic compounds according to the present invention, the compounds composed of only hydrocarbons belonging to group A have high molecular stability.

In compounds having substituents containing nitrogen atoms as compounds belonging to group B, the oxidation potentials of the molecules are significantly changed, or the intermolecular interactions are changed. A compound having a substituent containing a nitrogen atom can shift the maximum light emission wavelength to a longer wavelength. Alternatively, a compound having a substituent containing a nitrogen atom can be used in a high concentration of 100% as an electrode interface, an electron-transporting or hole-transporting hole-trap type light-emitting material, or a light-emitting material.

Among the organic compounds according to the present invention, particularly used are the compounds belonging to group A and compounds represented by the following Formula (2):

[Chem. 8]

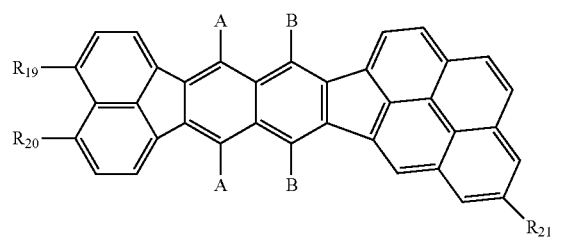

(2)

In Formula (2), $R_{19}$ and $R_{20}$ are each independently selected from hydrogen atoms, alkyl groups having 1 to 4 carbon atoms, and phenyl groups; either A or B is a phenyl group, and the other is a hydrogen atom; and $R_{21}$ is an alkyl group having 1 to 4 carbon atoms. The phenyl group may have an alkyl group having 1 to 4 carbon atoms.

As example compounds, compounds belonging to groups A and B have been mentioned. These compounds emit green light by their basic skeleton themselves. The organic compounds according to the present invention can emit light having a longer wavelength than that of green light, specifically, red light, by introducing substituents to the basic skeletons. In addition, the organic compound according to the present invention may be used as a host material of the light-emitting layer of an organic light-emitting device or may be used in an electron-transporting layer, an electron-injecting layer, a hole-transporting layer, a hole-injecting layer, or a hole blocking layer. In such cases, the color of light emitted by the organic light-emitting device is not limited. Furthermore, the organic compound according to the present invention can be used as an assist material of the light-emitting layer of an organic light-emitting device.

Description of Synthesis Route

An example of synthesis route of the organic compound according to the present invention will be described with reference to reaction formulae below. In a case of introducing a substituent to a desired position of the following formulae, the hydrogen atom at the position where the substituent is introduced is substituted with another substituent to perform synthesis. Examples of the substituent substituting for the hydrogen atom include alkyl groups, halogen atoms, and phenyl groups.

Synthesis Route 1

[Chem. 9]

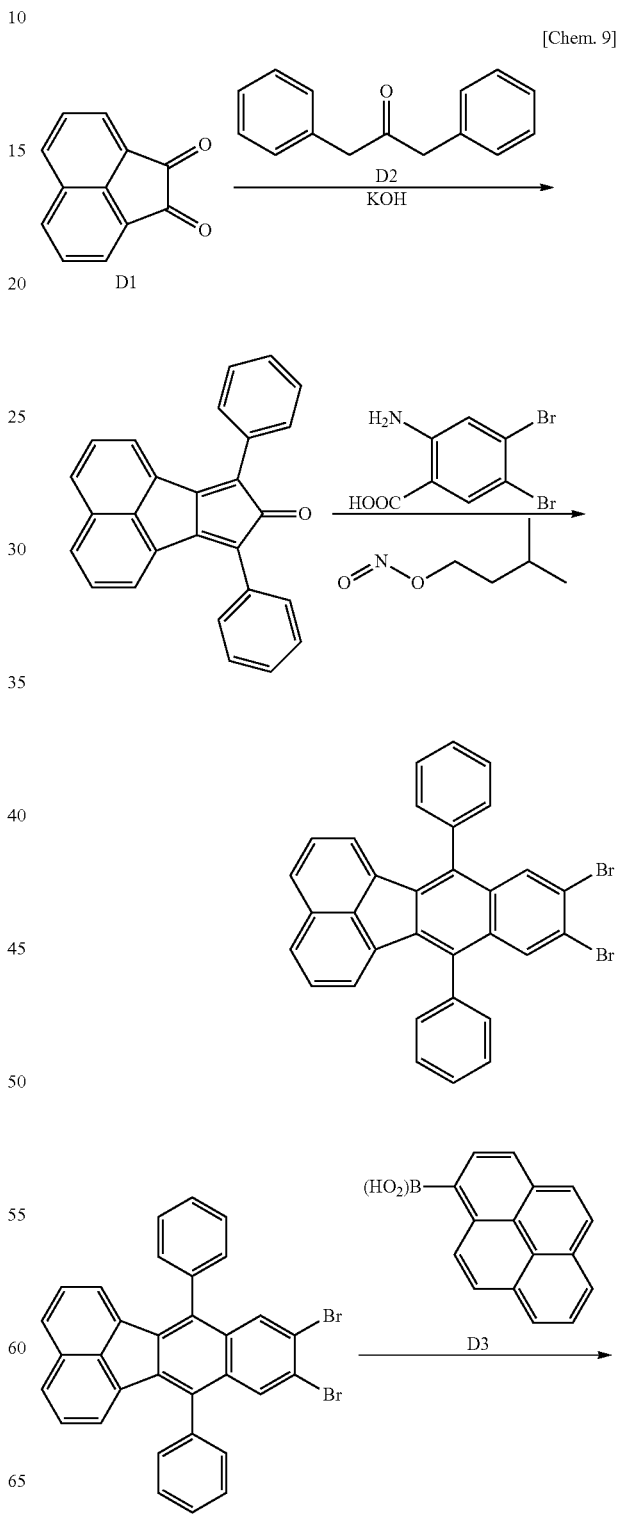

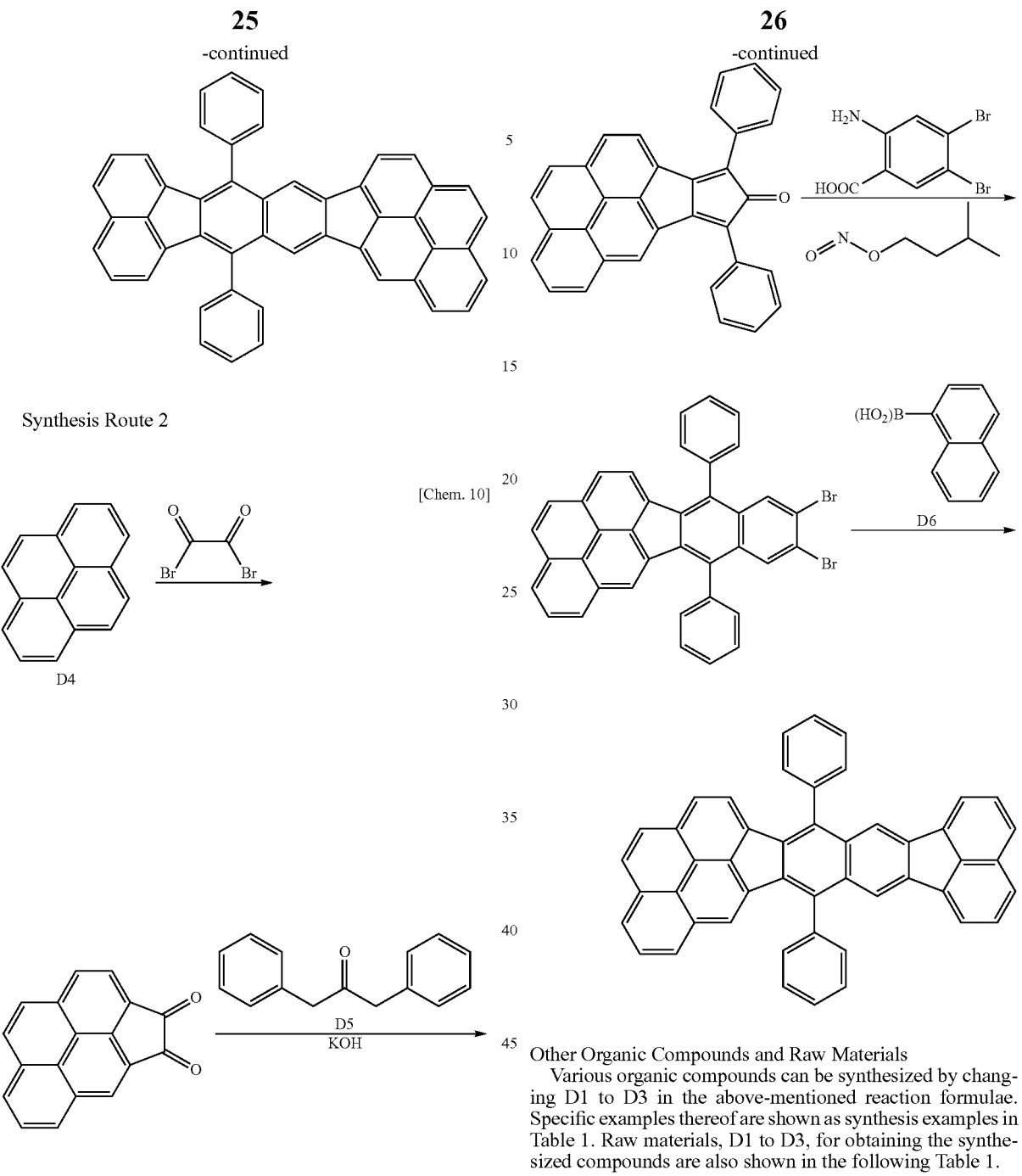
Other Organic Compounds and Raw Materials
Various organic compounds can be synthesized by changing D1 to D3 in the above-mentioned reaction formulae. Specific examples thereof are shown as synthesis examples in Table 1. Raw materials, D1 to D3, for obtaining the synthesized compounds are also shown in the following Table 1.
TABLE 1
| Synthesis Example | D1 | D2 | D3 |
|---|---|---|---|
| 1 | | | |

TABLE 1-continued
| | | | |
|---|---|---|---|
| 2 | 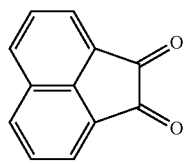 | 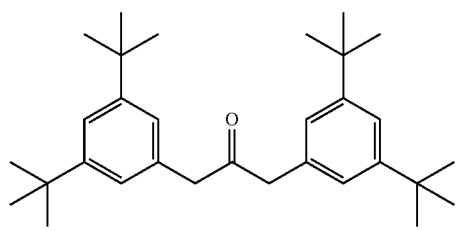 | 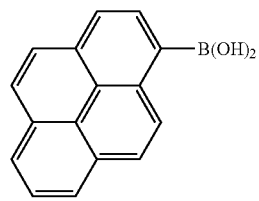 |
| 3 | 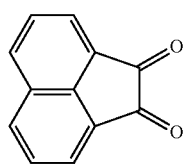 | 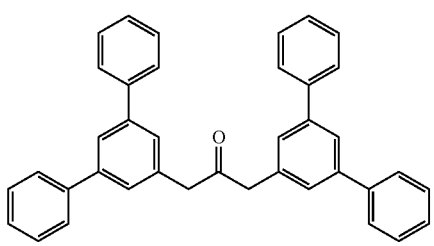 | 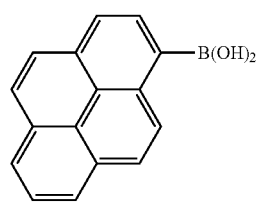 |
| 4 | 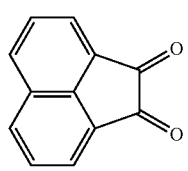 | 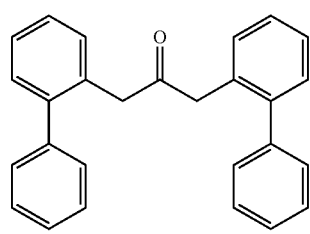 | 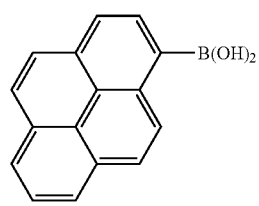 |
| 5 | 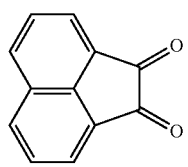 | 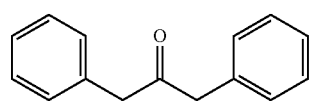 | 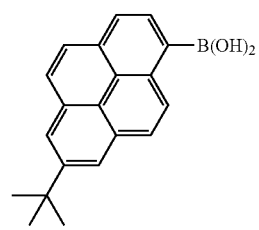 |
| 6 | 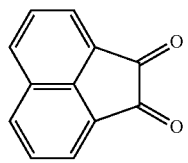 | 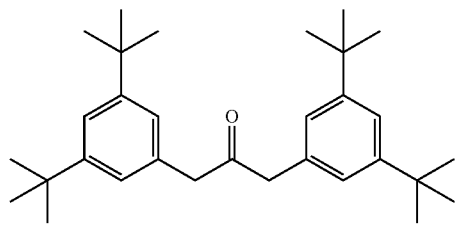 | 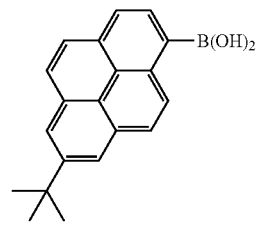 |
| 7 | 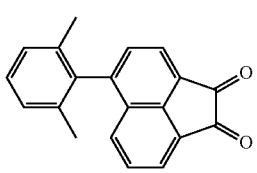 | 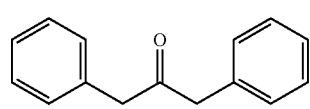 | 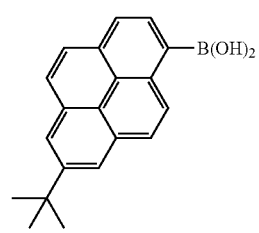 |

TABLE 1-continued
| 8 | 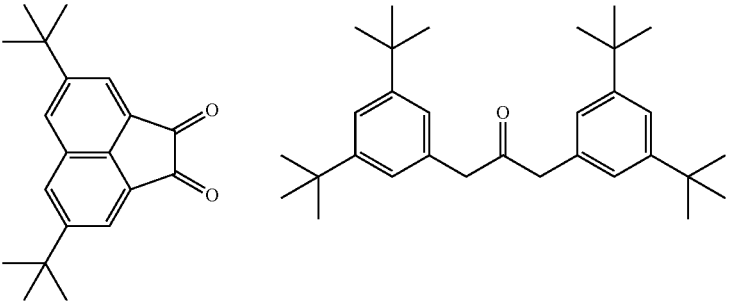 | | |
| Synthesis Example | Synthesized Compound | Example Compound No. |
|---|---|---|
| 1 | 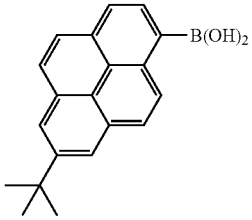 [SMILES: CC(C)(C)c1cc2ccc3ccc(B(O)O)c4ccc(c1)c2c34] | A2 |
| 2 | 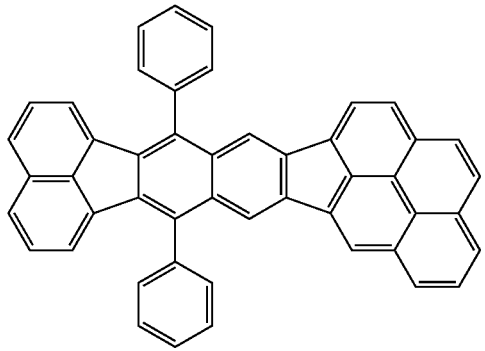 [SMILES: c1ccc(-c2c3cc4c(cc3c(-c3ccccc3)c3c5cccc6cccc(c23)c65)c2cc3cccc5ccc6ccc4c2c6c53)cc1] | A5 |

TABLE 1-continued
| 3 | 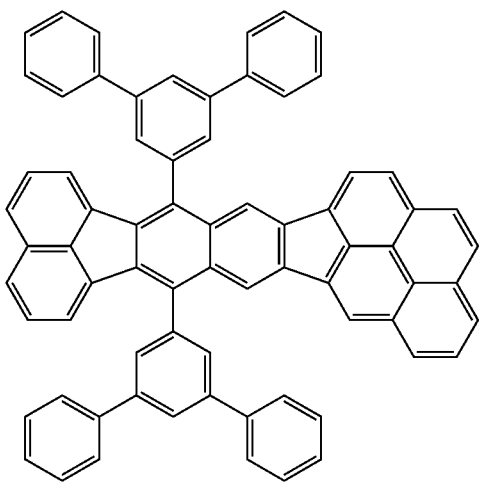 [SMILES: c1ccc(-c2cc(-c3ccccc3)cc(-c3c4cc5c(cc4c(-c4cc(-c6ccccc6)cc(-c6ccccc6)c4)c4c6cccc7cccc(c34)c76)c3cc4cccc6ccc7ccc5c3c7c64)c2)cc1] | A7 |
| 4 | 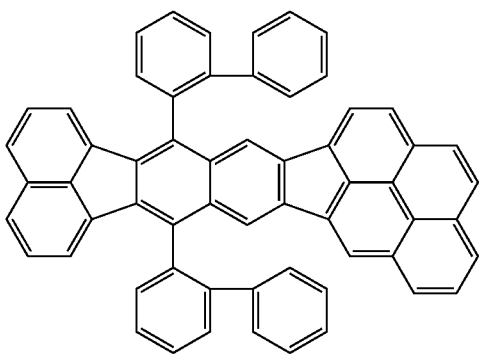 [SMILES: c1ccc(-c2ccccc2-c2c3cc4c(cc3c(-c3ccccc3-c3ccccc3)c3c5cccc6cccc(c23)c65)c2cc3cccc5ccc6ccc4c2c6c53)cc1] | A8 |
| 5 | 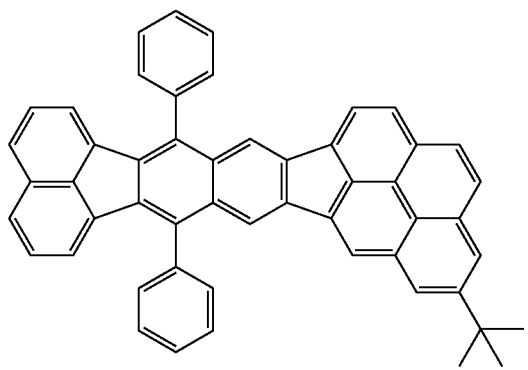 [SMILES: CC(C)(C)c1cc2ccc3ccc4c5cc6c(-c7ccccc7)c7c8cccc9cccc(c7c(-c7ccccc7)c6cc5c5cc(c1)c2c3c45)c98] | A11 |
| 6 | 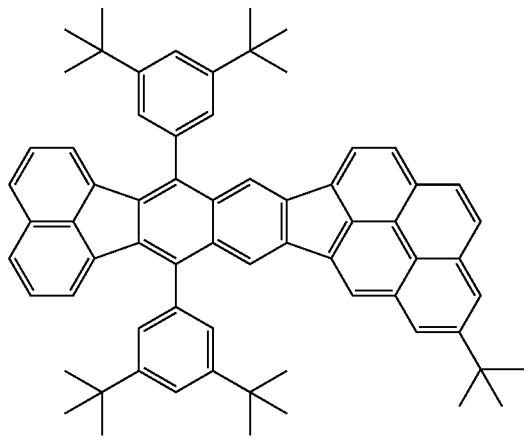 [SMILES: CC(C)(C)c1cc(-c2c3cc4c(cc3c(-c3cc(C(C)(C)C)cc(C(C)(C)C)c3)c3c5cccc6cccc(c23)c65)c2cc3cc(C(C)(C)C)cc5ccc6ccc4c2c6c53)cc(C(C)(C)C)c1] | A12 |

TABLE 1-continued
| | |
|---|---|
| 7 | A16 |
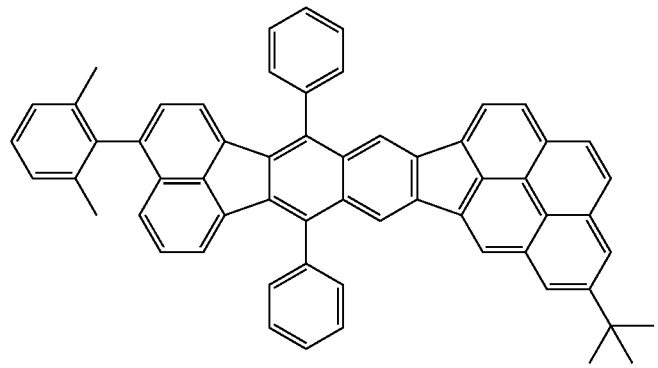 [SMILES: Cc1cccc(C)c1-c1ccc2c3c(-c4ccccc4)c4cc5c(cc4c(-c4ccccc4)c3c3cccc1c23)c1cc2cc(C(C)(C)C)cc3ccc4ccc5c1c4c32]
| | |
|---|---|
| 8 | A17 |
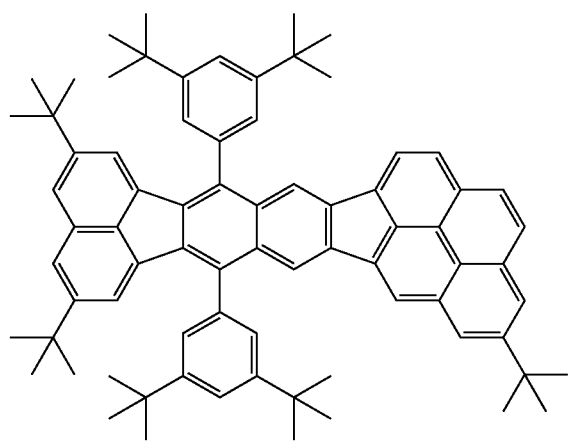 [SMILES: CC(C)(C)c1cc(-c2c3cc4c(cc3c(-c3cc(C(C)(C)C)cc(C(C)(C)C)c3)c3c5cc(C(C)(C)C)cc6cc(C(C)(C)C)cc(c23)c65)c2cc3cc(C(C)(C)C)cc5ccc6ccc4c2c6c53)cc(C(C)(C)C)c1]
Similarly, various organic compounds can be synthesized by changing D4 to D6 in the above-mentioned reaction formulae. Specific examples thereof are shown as synthesis examples in Table 2. Raw materials, D4 to D6, for obtaining the synthesized compounds are also shown in the following Table 2.
TABLE 2
| Example Compound No. | D4 | D5 | D6 |
|---|---|---|---|
| 9 | 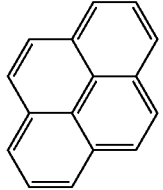 | 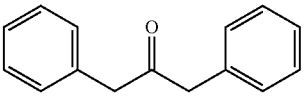 | 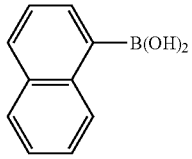 |
| 10 | 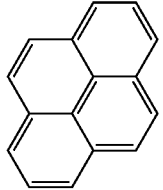 | 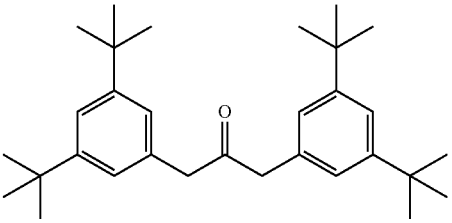 | 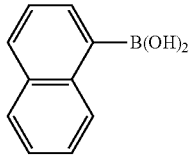 |

TABLE 2-continued
| | | | |
|---|---|---|---|
| 11 | 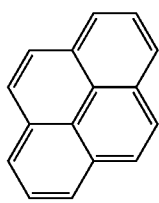 | 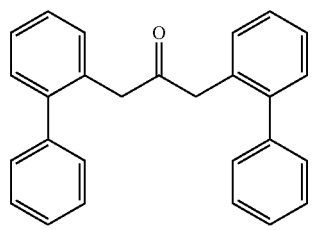 | 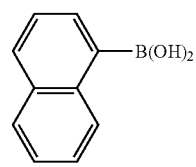 |
| 12 | 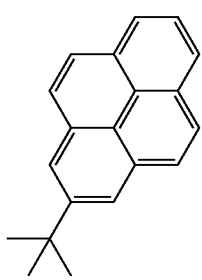 | 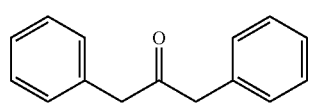 | 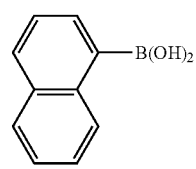 |
| 13 | 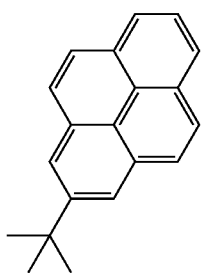 | 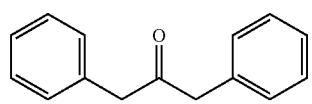 | 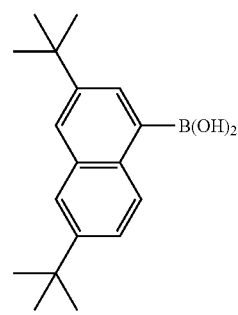 |
| 14 | 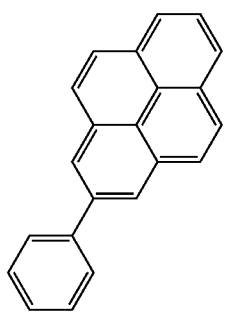 | 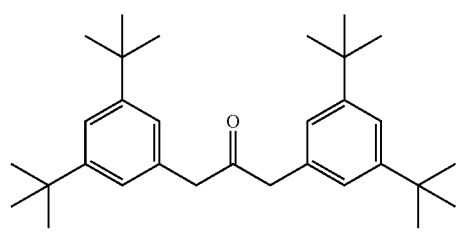 | 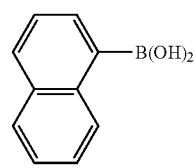 |
| Example Compound No. | Synthesized Compound | Example Compound No. |
|---|---|---|
| 9 | 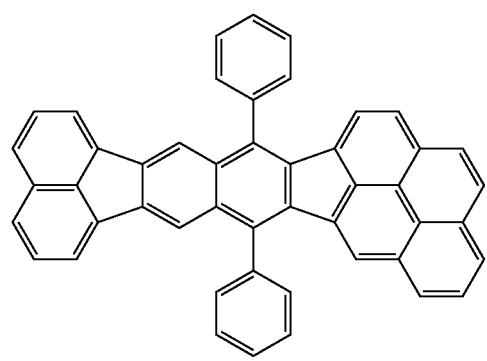 [SMILES: c1ccc(-c2c3cc4c(cc3c(-c3ccccc3)c3c5cc6cccc7ccc8ccc(c23)c5c8c76)c2cccc3cccc4c32)cc1] | A3 |

TABLE 2-continued
| 10 | 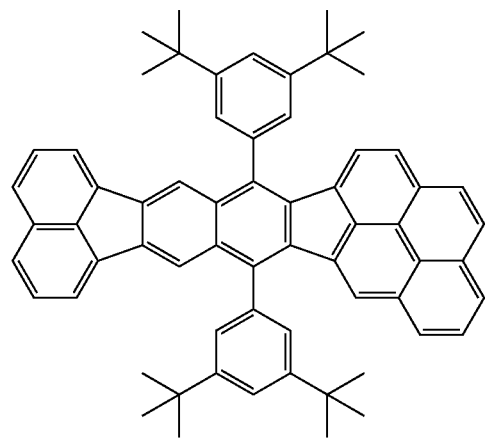 [SMILES: CC(C)(C)c1cc(-c2c3cc4c(cc3c(-c3cc(C(C)(C)C)cc(C(C)(C)C)c3)c3c5cc6cccc7ccc8ccc(c23)c5c8c76)c2cccc3cccc4c32)cc(C(C)(C)C)c1] | A25 |
| 11 | 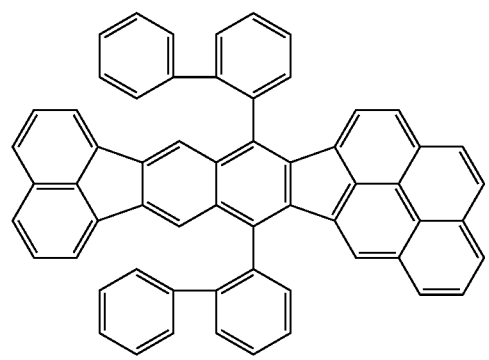 [SMILES: c1ccc(-c2ccccc2-c2c3cc4c(cc3c(-c3ccccc3-c3ccccc3)c3c5cc6cccc7ccc8ccc(c23)c5c8c76)c2cccc3cccc4c32)cc1] | A27 |
| 12 | 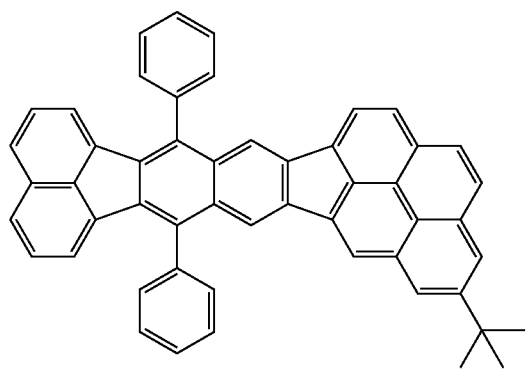 [SMILES: CC(C)(C)c1cc2ccc3ccc4c5cc6c(-c7ccccc7)c7c8cccc9cccc(c7c(-c7ccccc7)c6cc5c5cc(c1)c2c3c45)c98] | A31 |
| 13 | 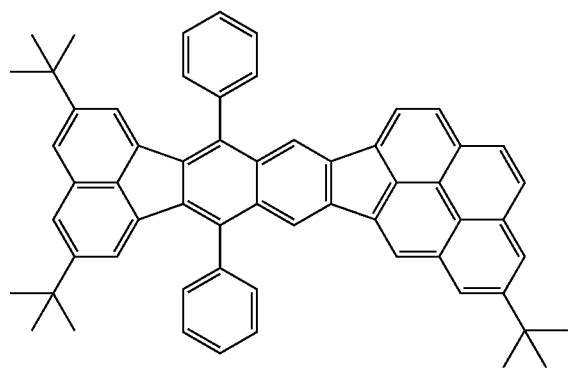 [SMILES: CC(C)(C)c1cc2ccc3ccc4c5cc6c(-c7ccccc7)c7c8cc(C(C)(C)C)cc9cc(C(C)(C)C)cc(c7c(-c7ccccc7)c6cc5c5cc(c1)c2c3c45)c98] | A33 |

TABLE 2-continued

| 14 | 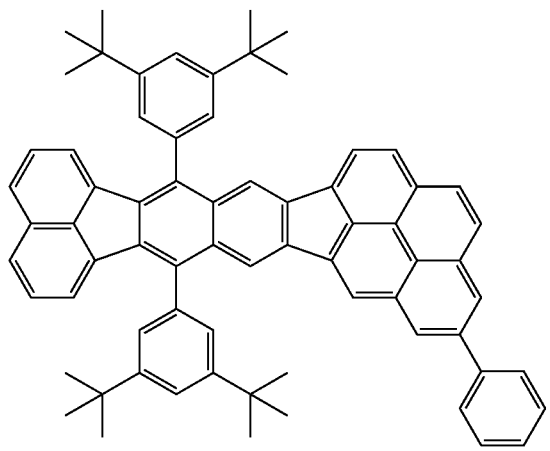 [SMILES: CC(C)(C)c1cc(-c2c3cc4c(cc3c(-c3cc(C(C)(C)C)cc(C(C)(C)C)c3)c3c5cccc6cccc(c23)c65)c2cc3cc(-c5ccccc5)cc5ccc6ccc4c2c6c53)cc(C(C)(C)C)c1] | A40 |

Description of Organic Light-Emitting Device

An organic light-emitting device according to this embodiment will be described.

The organic light-emitting device according to the embodiment includes a pair of electrodes of an anode and a cathode and an organic compound layer disposed between the electrodes. The organic compound layer is a device containing an organic compound according to the present invention.

In the organic light-emitting device according to the embodiment, the organic compound layer may be multi layers. Examples of the multi layers include a hole-injecting layer, a hole-transporting layer, a light-emitting layer, a hole blocking layer, an exciton blocking layer, an electron-transporting layer, and an electron-injecting layer. An appropriate combination of these layers can be used.

When the organic compound according to the embodiment is used as a guest material in the light-emitting layer, the concentration of the guest material is preferably 0.1 to 30 wt %, more preferably 0.5 to 10 wt %, based on the amount of the host materials.

The present inventors have conducted various investigations and have found that a device having a light-emitting layer containing the organic compound according to the present invention as a host material or a guest material, in particular, as a guest material outputs light with a high efficiency and high luminance.

The organic light-emitting device according to the embodiment can include, in addition to the organic compound according to the present invention, a known low molecular weight or high molecular weight hole-injecting material, hole-transporting material, host material, guest material, electron-injecting material, or electron-transporting material, as necessary.

Examples of these compounds are listed below.

As the material used in a hole-injecting layer or a hole-transporting layer, a material having a high hole mobility can be used. Examples of the low molecular weight or high molecular weight material having hole-injecting ability or hole-transporting ability include triarylamine derivatives, phenylenediamine derivatives, stilbene derivatives, phthalocyanine derivatives, porphyrine derivatives, poly(vinylcarbazole), poly(thiophene), and other electrically conductive polymers, but are not limited thereto.

Regarding the host material, Table 3 shows specific structures. The host material may be a derivative of the compounds shown by structural formulae shown in Table 3. Other examples of the host material include fused ring compounds (e.g., fluorene derivatives, naphthalene derivatives, anthracene derivatives, pyrene derivatives, carbazole derivatives, quinoxaline derivatives, and quinone derivatives); organic aluminum complexes such as tris(8-quinolinolato) aluminum; organic zinc complexes; and polymer derivatives such as triphenylamine derivatives, poly(fluorene) derivatives, and poly(phenylene) derivatives, but are not limited thereto.

TABLE 3

| H1 | 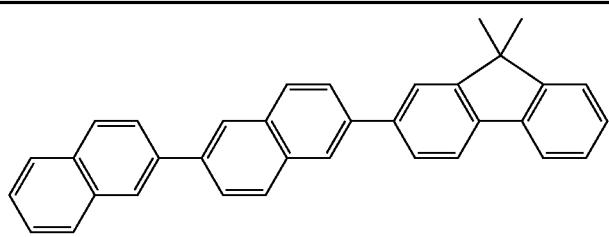 |
| H2 | 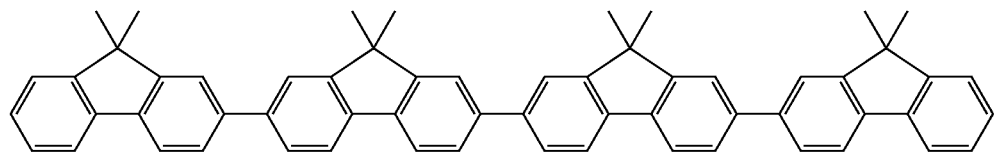 [SMILES: CC1(C)c2ccccc2-c2ccc(-c3ccc4c(c3)C(C)(C)c3cc(-c5ccc6c(c5)C(C)(C)c5cc(-c7ccc8c(c7)C(C)(C)c7ccccc7-8)ccc5-6)ccc3-4)cc21] |

TABLE 3-continued
H3 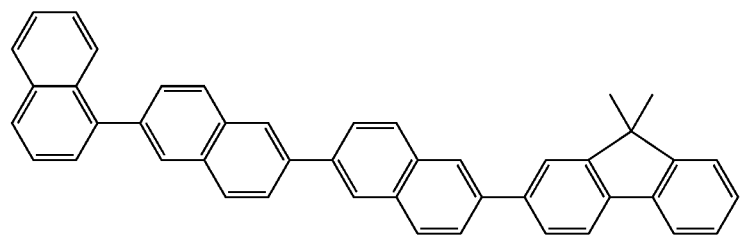 [SMILES: CC1(C)c2ccccc2-c2ccc(-c3ccc4cc(-c5ccc6cc(-c7cccc8ccccc78)ccc6c5)ccc4c3)cc21]
H4 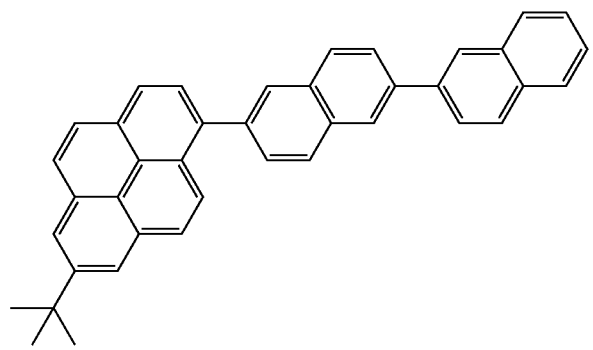 [SMILES: CC(C)(C)c1cc2ccc3ccc(-c4ccc5cc(-c6ccc7ccccc7c6)ccc5c4)c4ccc(c1)c2c34]
H5 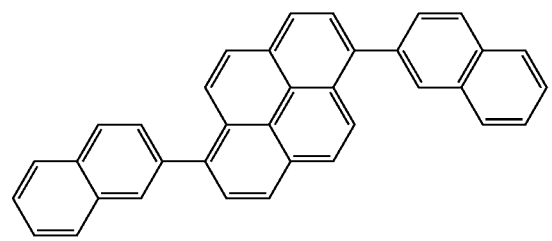 [SMILES: c1ccc2cc(-c3ccc4ccc5c(-c6ccc7ccccc7c6)ccc6ccc3c4c65)ccc2c1]
H6 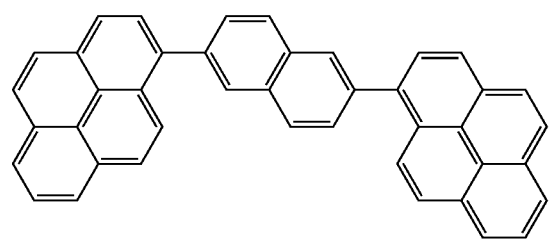 [SMILES: c1cc2ccc3ccc(-c4ccc5cc(-c6ccc7ccc8cccc9ccc6c7c89)ccc5c4)c4ccc(c1)c2c34]
H7 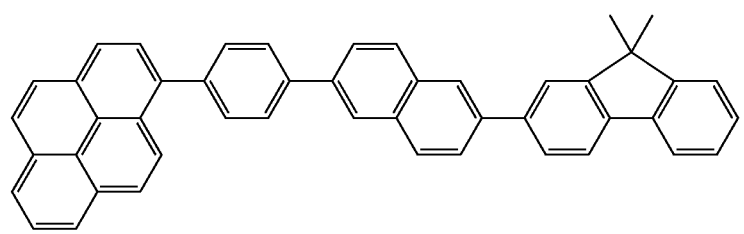 [SMILES: CC1(C)c2ccccc2-c2ccc(-c3ccc4cc(-c5ccc(-c6ccc7ccc8cccc9ccc6c7c89)cc5)ccc4c3)cc21]

TABLE 3-continued
H8
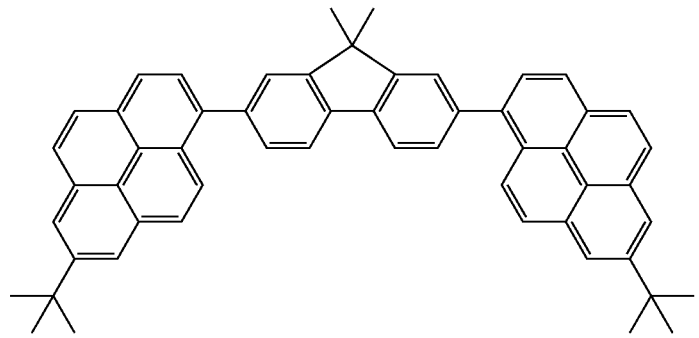 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34]
H9
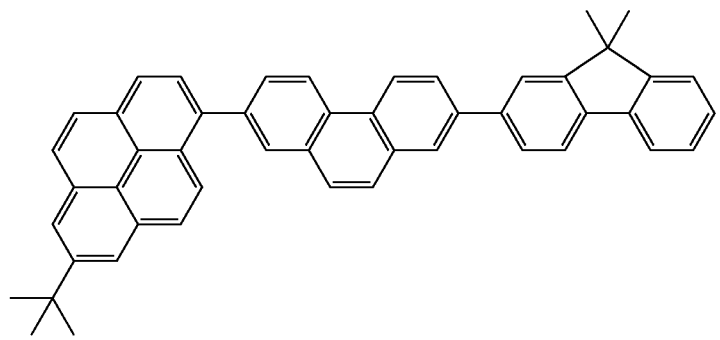 [SMILES: CC(C)(C)c1cc2ccc3ccc(-c4ccc5c(ccc6cc(-c7ccc8c(c7)C(C)(C)c7ccccc7-8)ccc65)c4)c4ccc(c1)c2c34]
H10
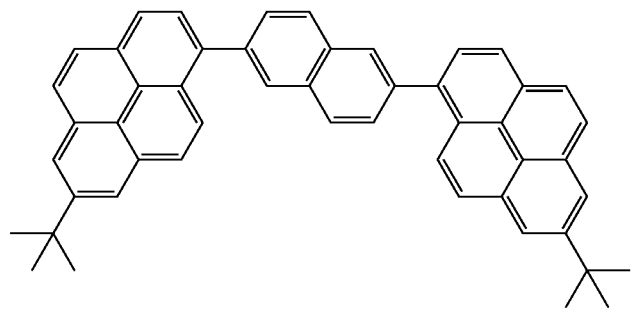 [SMILES: CC(C)(C)c1cc2ccc3ccc(-c4ccc5cc(-c6ccc7ccc8cc(C(C)(C)C)cc9ccc6c7c89)ccc5c4)c4ccc(c1)c2c34]
H11
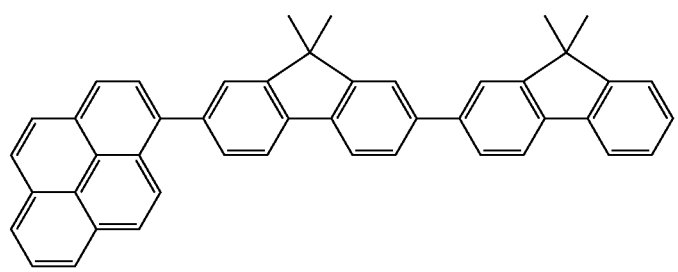 [SMILES: CC1(C)c2ccccc2-c2ccc(-c3ccc4c(c3)C(C)(C)c3cc(-c5ccc6ccc7cccc8ccc5c6c78)ccc3-4)cc21]
H12
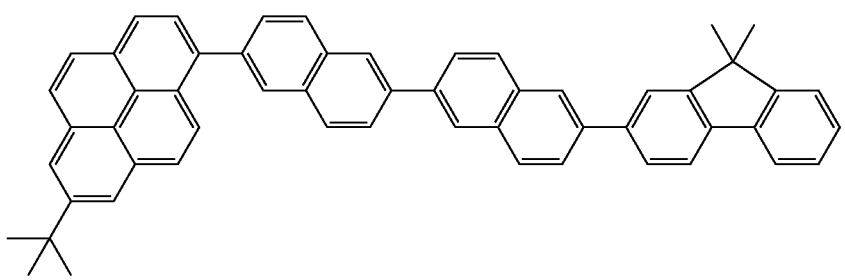 [SMILES: CC(C)(C)c1cc2ccc3ccc(-c4ccc5cc(-c6ccc7cc(-c8ccc9c(c8)C(C)(C)c8ccccc8-9)ccc7c6)ccc5c4)c4ccc(c1)c2c34]

TABLE 3-continued
H13
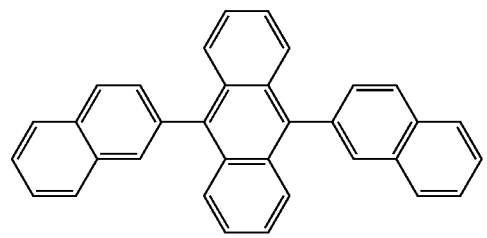 [SMILES: c1ccc2cc(-c3c4ccccc4c(-c4ccc5ccccc5c4)c4ccccc34)ccc2c1]
H14
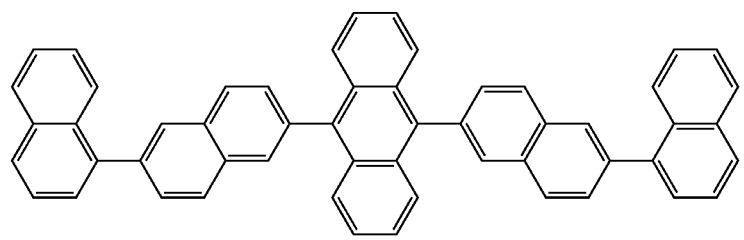 [SMILES: c1ccc2c(-c3ccc4cc(-c5c6ccccc6c(-c6ccc7cc(-c8cccc9ccccc89)ccc7c6)c6ccccc56)ccc4c3)cccc2c1]
H15
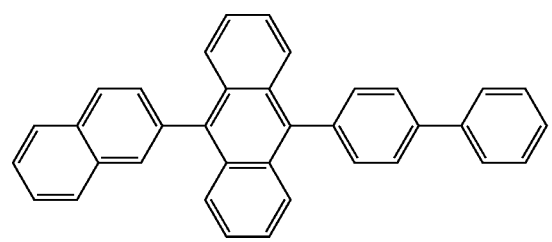 [SMILES: c1ccc(-c2ccc(-c3c4ccccc4c(-c4ccc5ccccc5c4)c4ccccc34)cc2)cc1]
H16
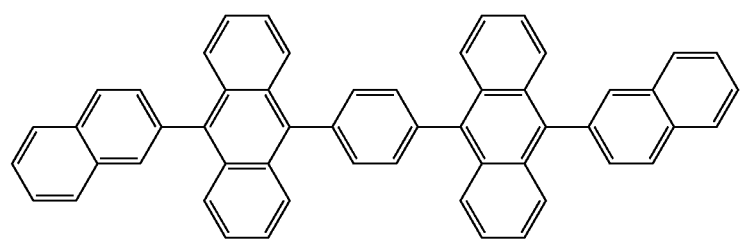 [SMILES: c1ccc2cc(-c3c4ccccc4c(-c4ccc(-c5c6ccccc6c(-c6ccc7ccccc7c6)c6ccccc56)cc4)c4ccccc34)ccc2c1]
H17
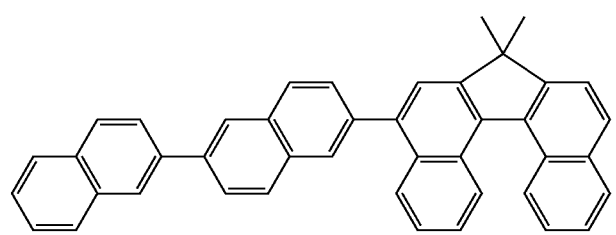 [SMILES: CC1(C)c2ccc3ccccc3c2-c2c1cc(-c1ccc3cc(-c4ccc5ccccc5c4)ccc3c1)c1ccccc21]

TABLE 3-continued
H18
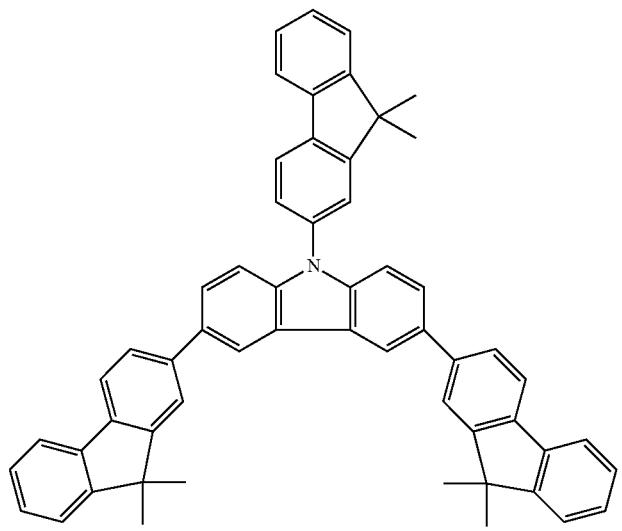 [SMILES: CC1(C)c2ccccc2-c2ccc(-c3ccc4c(c3)c3cc(-c5ccc6c(c5)C(C)(C)c5ccccc5-6)ccc3n4-c3ccc4c(c3)C(C)(C)c3ccccc3-4)cc21]
H19
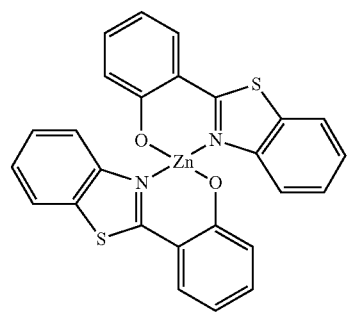
H20
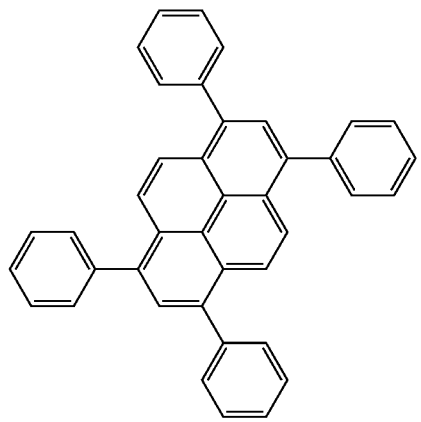 [SMILES: c1ccc(-c2cc(-c3ccccc3)c3ccc4c(-c5ccccc5)cc(-c5ccccc5)c5ccc2c3c54)cc1]
H21
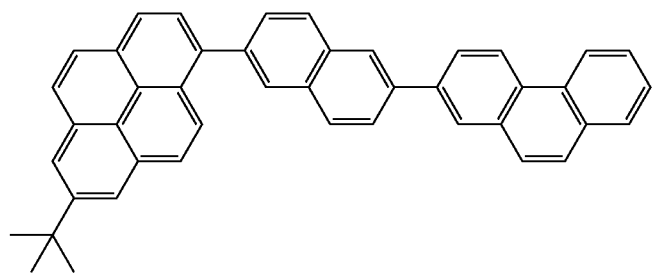 [SMILES: CC(C)(C)c1cc2ccc3ccc(-c4ccc5cc(-c6ccc7c(ccc8ccccc87)c6)ccc5c4)c4ccc(c1)c2c34]

TABLE 3-continued
H22 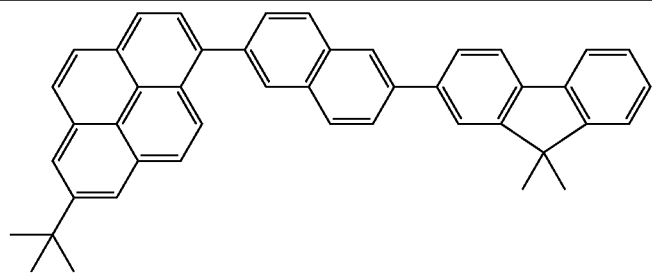
H23 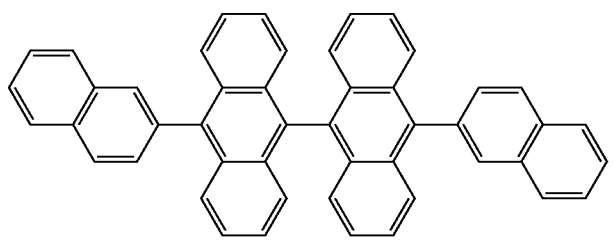 [SMILES: c1ccc2cc(-c3c4ccccc4c(-c4c5ccccc5c(-c5ccc6ccccc6c5)c5ccccc45)c4ccccc34)ccc2c1]
H24 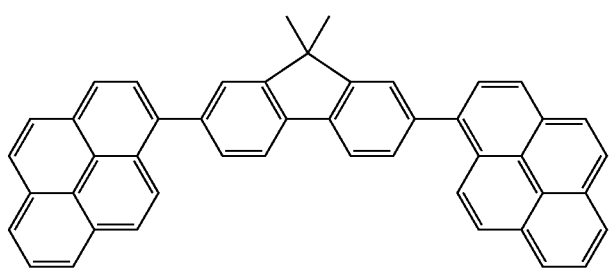 [SMILES: CC1(C)c2cc(-c3ccc4ccc5cccc6ccc3c4c56)ccc2-c2ccc(-c3ccc4ccc5cccc6ccc3c4c56)cc21]
H25 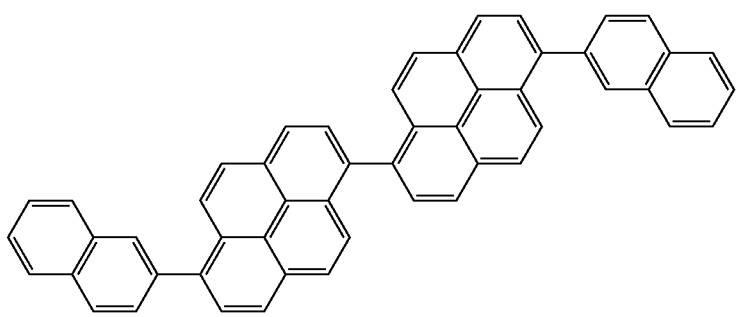 [SMILES: c1ccc2cc(-c3ccc4ccc5c(-c6ccc7ccc8c(-c9ccc%10ccccc%10c9)ccc9ccc6c7c98)ccc6ccc3c4c65)ccc2c1]
H26 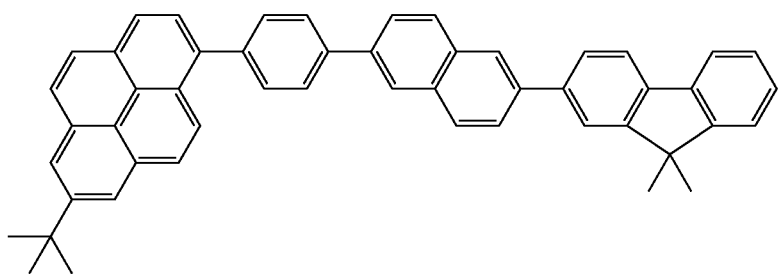 [SMILES: CC(C)(C)c1cc2ccc3ccc(-c4ccc(-c5ccc6cc(-c7ccc8c(c7)C(C)(C)c7ccccc7-8)ccc6c5)cc4)c4ccc(c1)c2c34]
H27 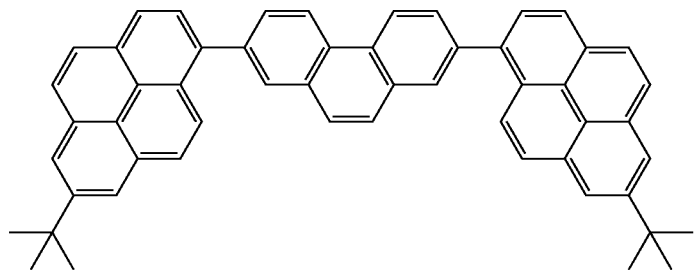 [SMILES: CC(C)(C)c1cc2ccc3ccc(-c4ccc5c(ccc6cc(-c7ccc8ccc9cc(C(C)(C)C)cc%10ccc7c8c9%10)ccc65)c4)c4ccc(c1)c2c34]

TABLE 3-continued

H28

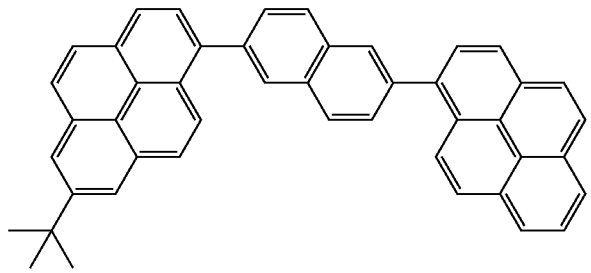 [SMILES: CC(C)(C)c1cc2ccc3ccc(-c4ccc5cc(-c6ccc7ccc8cccc9ccc6c7c89)ccc5c4)c4ccc(c1)c2c34]

The electron-injecting material or the electron-transporting material is selected by considering, for example, balance with the hole mobility of the hole-injecting material or the hole-transporting material. Examples of the material having electron injecting ability or electron transporting ability include oxadiazole derivatives, oxazole derivatives, pyrazine derivatives, triazole derivatives, triazine derivatives, quinoline derivatives, quinoxaline derivatives, phenanthroline derivatives, and organic aluminum complexes, but are not limited thereto.

As the material for the anode, materials having high work functions can be used, and examples thereof include simple metals such as gold, platinum, silver, copper, nickel, palladium, cobalt, selenium, vanadium, and tungsten and alloys thereof; and metal oxides such as tin oxide, zinc oxide, indium oxide, indium tin oxide (ITO), and indium zinc oxide. In addition, the material may be an electrically conductive polymer such as polyaniline, polypyrrole, or polythiophene. These electrode materials may be used alone or in a combination of two or more thereof. The anode may have a monolayer structure or a multi-layer structure.

On the other hand, as the material for the cathode, materials having low work functions can be used, and examples thereof include alkali metals such as lithium; alkali earth metals such as calcium; simple metals such as aluminum, titanium, manganese, silver, lead, and chromium; and alloys of combinations of these simple metals, such as magnesium-silver, aluminum-lithium, and aluminum-magnesium. In addition, metal oxides such as indium tin oxide (ITO) can be used. These electrode materials may be used alone or in a combination of two or more thereof. The cathode may have a monolayer structure or a multi-layer structure.

In the organic light-emitting device according to the embodiment, a layer containing an organic compound according to the present invention and a layer composed of another organic compound are formed by the following process. In usual, the layers are formed by vacuum deposition, ionized vapor deposition, sputtering, plasma coating, or known coating (e.g., spin coating, dipping, casting, an LB method, or an ink-jetting method) of a compound dissolved in an appropriate solvent. Herein, when the layer is formed by vacuum deposition, solution coating, or the like, crystallization, etc. hardly occur, and the layer is excellent in temporal stability. Furthermore, in the formation by coating, the film may be formed of a combination with an appropriate binder resin.

Examples of the binder resin include polyvinyl carbazole resins, polycarbonate resins, polyester resins, ABS resins, acrylic resins, polyimide resins, phenol resins, epoxy resins, silicone resins, and urea resins, but are not limited thereto. These binder resins may be used alone or in a combination of two or more thereof as a homopolymer or a copolymer. In addition, a known additive, such as a plasticizer, an antioxidant, or a UV absorber, may be used with the binder resin, as necessary.

Display Apparatus Including Organic Light-Emitting Device

Application of the organic light-emitting device according to the present invention will be described below.

The organic light-emitting device according to the present invention can be used in display apparatuses and lighting systems. Other application includes exposure light sources of electrophotographic image forming apparatuses and backlights of liquid crystal display apparatuses.

The display apparatus includes the organic light-emitting device according to the present invention in its display. This display includes a plurality of pixels, and the pixels each include an organic light-emitting device according to the present invention and a TFT device of an example of switching devices. The anode or the cathode of the organic light-emitting device is electrically connected to the drain electrode or the source electrode of the TFT device. The display apparatus can be used as an image display apparatus of, for example, a personal computer. The display apparatus may be an image input apparatus by being further provided with an image input portion.

The image input apparatus includes an image input portion for inputting information from, for example, an area CCD, a linear CCD, or memory card and a display portion for displaying the input information. The image input apparatus forms an imaging apparatus such as a digital camera by being further provided with an imaging optical system. The display portion of an imaging apparatus or an ink-jet printer may include both an image output function for displaying an image based on image information input from the outside and an input function for inputting processed information into an image as an operation panel. The display apparatus may be used in a display portion of a multi-functional printer.

Then, a display apparatus including the organic light-emitting device according to the present invention will be described.

FIG. 1 is a schematic cross-sectional view of a display apparatus including organic light-emitting devices according to the present invention and TFT devices as an example of switching devices for controlling light emission/non-emission or light emission luminance of the organic light-emitting devices. This figure shows two pairs of the organic light-emitting device and the TFT device. The display apparatus may further include a transistor (not shown) for controlling the light emission luminance. The display apparatus performs display by driving the switching devices according to information to turn on or off the organic light-emitting device, and information is thereby displayed. The structure will be described in detail below.

The display apparatus of FIG. 1 includes a substrate 1 made of, for example, glass and, on the substrate 1, a moisture proof film 2 for protecting TFT devices or an organic compound layer. Here, reference sign 3 denotes a metal gate electrode, reference sign 4 denotes a gate insulating film, and reference sign 5 denotes a semi-conductor layer.

The TFT device 8 includes a semi-conductor layer 5, a drain electrode 6, and a source electrode 7. In the upper portion of the TFT device 8, an insulating film 9 is disposed. The anode 11 of an organic light-emitting device is connected to the source electrode 7 via a contact hole 10. The structure of the display apparatus is not limited to this, and either the anode or the cathode may be connected to either the source electrode or the drain electrode of the TFT device.

The organic compound layer 12 is composed of multiple layers, but is drawn as a single layer in this figure. On the cathode 13, a first protection layer 14 and a second protection layer 15 are disposed for inhibiting deterioration of the organic light-emitting device.

EXAMPLES

Example 1

Synthesis of Example Compound A2

[Chem. 11]

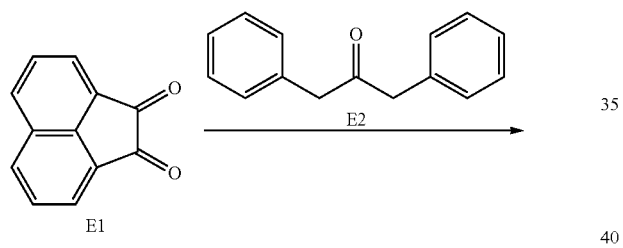

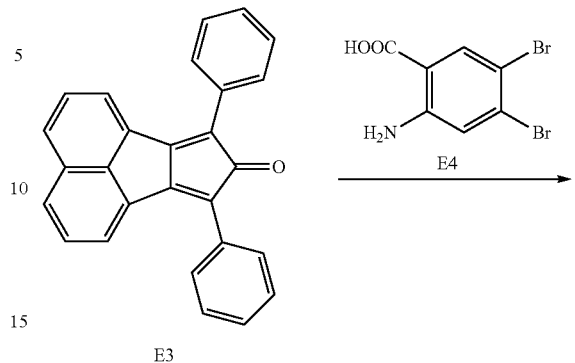

[Chem. 12]

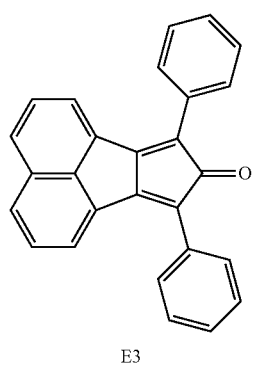

E3

E1 (9.1 g, 50 mmol) and E2 (10.5 g, 50 mmol) were put in 200 mL of ethanol. The mixture was heated to 60° C., and 20 mL of an aqueous solution of 5 M sodium hydroxide was dropwise added to the mixture. After completion of the dropping, the mixture was heated to 80° C., followed by stirring for 2 hours. Then, after cooling, the precipitate was collected by filtration, was washed with water and ethanol, and was dried under reduced pressure by heating at 80° C. to obtain 16 g (yield: 90%) of a green solid of E3.

Then, E3 (3.6 g, 10 mmol) and E4 (3.2 g, 11 mmol) were put in 100 mL of toluene. The mixture was heated to 80° C., and isoamyl nitrite (1.3 g, 11 mmol) was gradually dropped into the mixture, followed by stirring at 110° C. for 3 hours. Then, after cooling, the reaction product was washed with water twice (100 mL×2). The resulting organic layer was washed with saturated brine and was dried over magnesium sulfate. The resulting solution was filtered, and the filtrate was concentrated to obtain a dark brown liquid. This liquid was purified by column chromatography (toluene/heptane=1:1) and was then recrystallized from chloroform/ethanol to obtain 4.32 g (yield: 77%) of a yellow crystal of E5.

[Chem. 13]

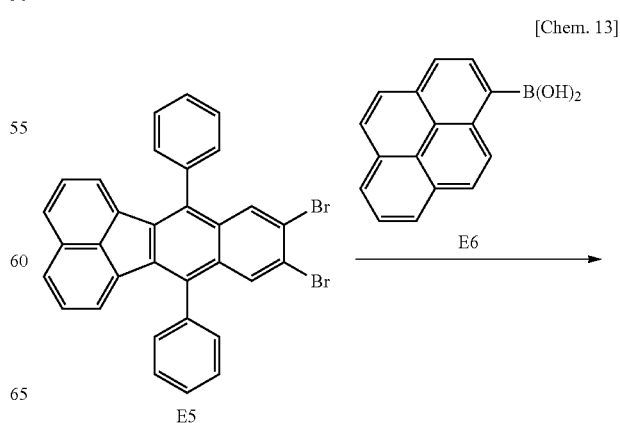

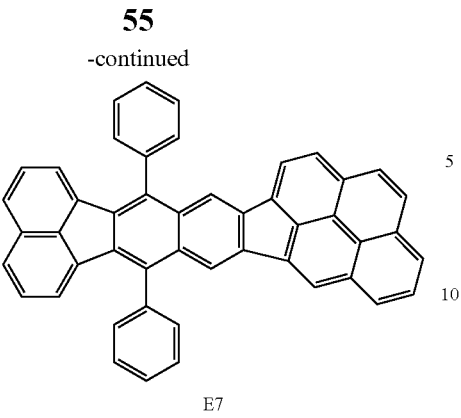

E7

Then, E5 (2.81 g, 5 mmol), 1-pyreneboronic acid (1.5 g, 10 mmol), tris(dibenzylideneacetone)dipalladium(0) (910 mg, 1.0 mmol), tricyclohexylphosphine (1 g, 3.0 mmol), diazabicycloundecene (7.5 mL), and dimethylformamide (50 mL) were heated until reflux occurs, followed by stirring 6 hours. After cooling, 20 mL of methanol was added to the mixture, and the precipitate was collected by filtration. This powder was dissolved in 50 mL of chloroform and was washed with water twice (100 mL×2). The resulting organic layer was washed with saturated brine and was dried over magnesium sulfate. The resulting solution was filtered, and the filtrate was concentrated to obtain a yellow liquid. This liquid was purified by column chromatography (toluene/heptane=1:4) and was then recrystallized from chloroform/methanol to obtain 1.66 g (yield: 55%) of a yellow crystal of example compound A2.

An emission spectrum of a toluene solution containing $1 \times 10^{-5}$ mol/L of example compound A2 was obtained by measuring photoluminescence at an excitation wavelength of 350 nm using F-4500 manufactured by Hitachi Ltd. The spectrum had a maximum emission peak at 489 nm.

Example 2

Synthesis of Example Compound A3

[Chem. 14]

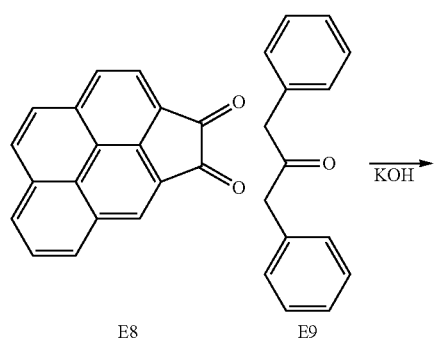

E8  E9

E8 (12.8 g, 50 mmol) and E9 (10.5 g, 50 mmol) were put in 200 mL of ethanol. The mixture was heated to 60° C., and 20 mL of an aqueous solution of 5 M sodium hydroxide was dropwise added to the mixture. After completion of the dropping, the mixture was heated to 80° C., followed by stirring for 2 hours. Then, after cooling, the precipitate was collected by filtration, was washed with water and ethanol, and was dried under reduced pressure by heating at 80° C. to obtain 18 g (yield: 85%) of a green solid of E6.

[Chem. 15]

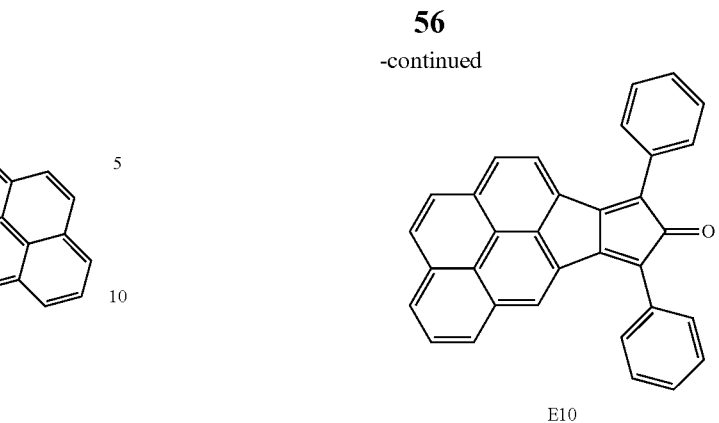

E10

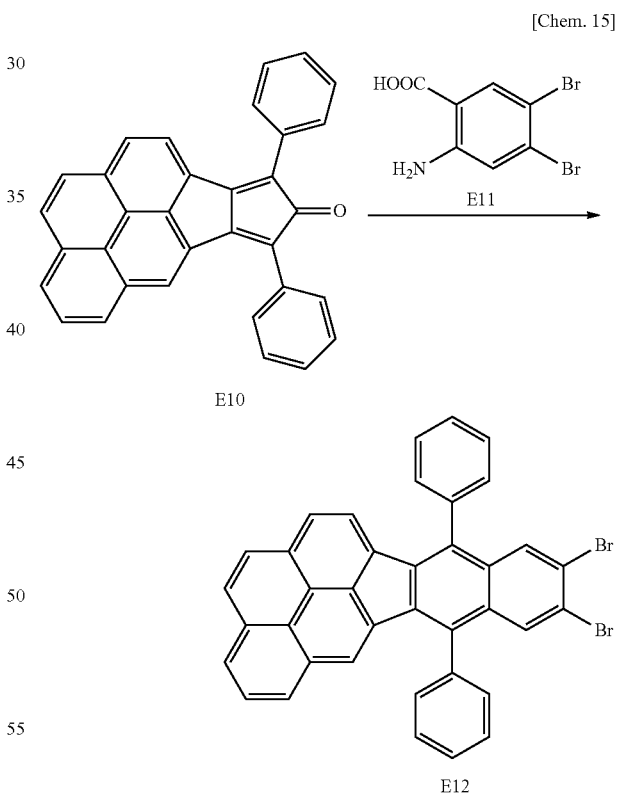

E12

Then, E10 (4.3 g, 10 mmol) and E11 (3.2 g, 11 mmol) were put in 100 mL of toluene. The mixture was heated to 80° C., and isoamyl nitrite (1.3 g, 11 mmol) was gradually dropped into the mixture, followed by stirring at 110° C. for 5 hours. Then, after cooling, the reaction product was washed with water twice (100 mL×2). The resulting organic layer was washed with saturated brine and was dried over magnesium sulfate. The resulting solution was filtered, and the filtrate was concentrated to obtain a dark brown liquid. This liquid was purified by column chromatography (toluene/heptane=1:1) and was then recrystallized from chloroform/ethanol to obtain 5.4 g (yield: 85%) of a yellow crystal of E12.

[Chem. 16]

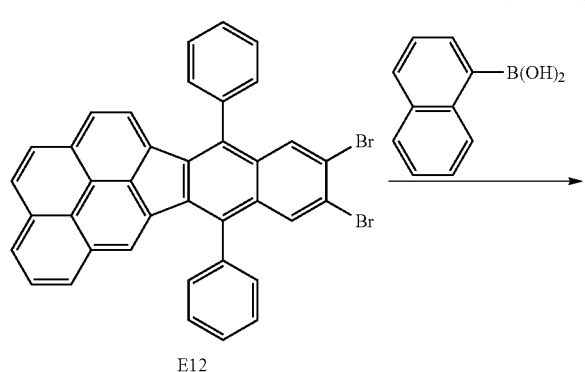

E12

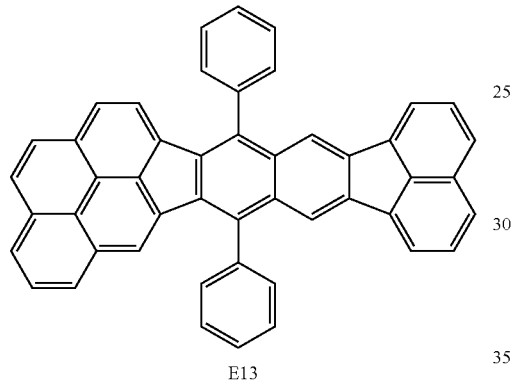

E13

Then, E9 (6 mg, 1.0 mmol), 1,8-diiodonaphthalene (456 mg, 1.2 mmol), tris(dibenzylideneacetone)dipalladium(0) (91 mg, 0.1 mmol), tricyclohexylphosphine (100 mg, 0.3 mmol), diazabicycloundecene (0.75 mL), and dimethylformamide (5 mL) were heated until reflux occurs, followed by stirring for 12 hours. After cooling, 20 mL of chloroform was added to the mixture, and the filtrate was washed with water twice (100 mL×2). The resulting organic layer was washed with saturated brine and was dried over magnesium sulfate. The resulting solution was filtered, and the filtrate was concentrated to obtain a yellow liquid. This liquid was purified by column chromatography (toluene/heptane=1:8) and was then recrystallized from chloroform/methanol to obtain 289 mg (yield: 48%) of a yellow crystal of example compound A3.

An emission spectrum of a toluene solution containing $1\times10^{-5}$ mol/L of example compound A3 was obtained by measuring photoluminescence at an excitation wavelength of 350 nm using F-4500 manufactured by Hitachi Ltd. The spectrum had a maximum emission peak at 489 nm.

Example 3

Synthesis of Example Compound A5

Example compound A5 was prepared by the same reaction and purification processes as those in Example 1 except that E14 was used instead of organic compound E2 used in Example 1.

[Chem. 17]

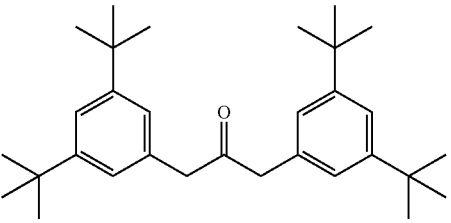

An emission spectrum of a toluene solution containing $1\times10^{-5}$ mol/L of example compound A5 was obtained by measuring photoluminescence at an excitation wavelength of 350 nm using F-4500 manufactured by Hitachi Ltd. The spectrum had a maximum emission peak at 490 nm.

Example 4

Synthesis of Example Compound A12

Example compound A12 was prepared by the same reaction and purification processes as those in Example 1 except that E14 and E15 were respectively used instead of organic compound E2 and 1-pyreneboronic acid used in Example 1.

[Chem. 18]

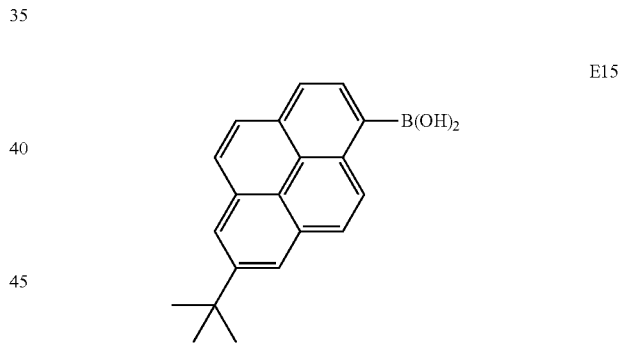

An emission spectrum of a toluene solution containing $1\times10^{-5}$ mol/L of example compound A12 was obtained by measuring photoluminescence at an excitation wavelength of 350 nm using F-4500 manufactured by Hitachi Ltd. The spectrum had a maximum emission peak at 495 nm.

Example 5

Synthesis of Example Compound A16

Example compound A16 was prepared by the same reaction and purification processes as those in Example 1 except that E16 and E15 were respectively used instead of organic compound E1 and 1-pyreneboronic acid used in Example 1.

[Chem. 19]

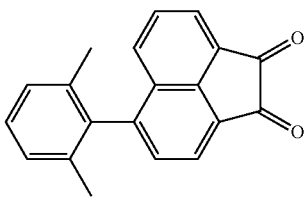

E16

An emission spectrum of a toluene solution containing 1×10$^{-5}$ mol/L of example compound A16 was obtained by measuring photoluminescence at an excitation wavelength of 350 nm using F-4500 manufactured by Hitachi Ltd. The spectrum had a maximum emission peak at 498 nm.

Example 6

Synthesis of Example Compound A27

Example compound A27 was prepared by the same reaction and purification processes as those in Example 2 except that E17 was used instead of organic compound E9 used in Example 2.

[Chem. 20]

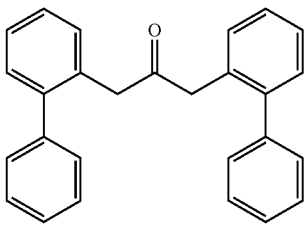

E17

An emission spectrum of a toluene solution containing 1×10$^{-5}$ mol/L of example compound A27 was obtained by measuring photoluminescence at an excitation wavelength of 350 nm using F-4500 manufactured by Hitachi Ltd. The spectrum had a maximum emission peak at 490 nm.

Example 7

Synthesis of Example Compound A33

Example compound A33 was prepared by the same reaction and purification processes as those in Example 2 except that E18 and E19 were respectively used instead of organic compound E8 and 1-naphthaleneboronic acid used in Example 2.

[Chem. 21]

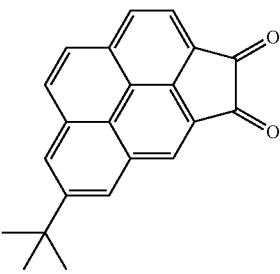

E18

[Chem. 22]

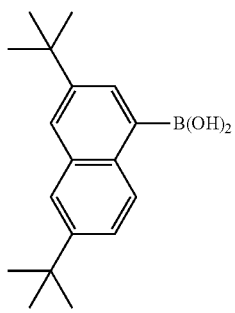

E19

An emission spectrum of a toluene solution containing 1×10$^{-5}$ mol/L of example compound A33 was obtained by measuring photoluminescence at an excitation wavelength of 350 nm using F-4500 manufactured by Hitachi Ltd. The spectrum had a maximum emission peak at 502 nm.

Examples 8 to 14

In these examples, organic light-emitting devices each having a structure of sequentially laminated (anode)/(hole-injecting layer)/(hole-transporting layer)/(light-emitting layer)/(hole/exciton blocking layer)/(electron-transporting layer)/(cathode) were produced. ITO (thickness: 100 nm) was patterned on a glass substrate. On the resulting ITO substrate, the following organic layers and electrode layers were sequentially formed by vacuum deposition by resistance heating in a vacuum chamber of 10$^{-5}$ Pa so that the facing area of the electrodes is 3 mm$^2$.

hole-transporting layer (40 nm): G-1 light-emitting layer (30 nm): compound H8 (host), example compound A2 (guest, weight ratio: 5%)

hole/exciton blocking layer (10 nm): G-3 electron-transporting layer (30 nm): G-4 metal electrode layer 1 (1 nm): LiF metal electrode layer 2 (100 nm): Al

[Chem. 23]

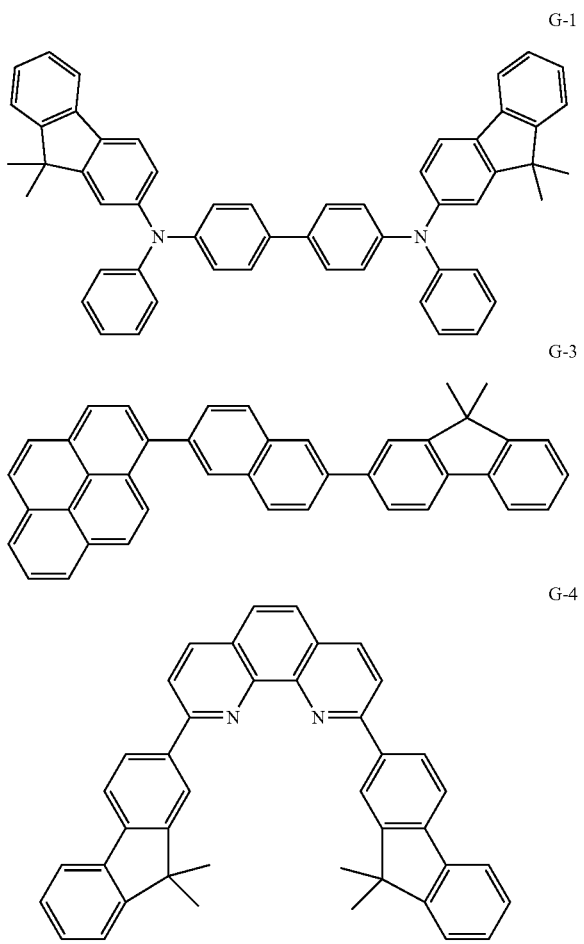

G-1

G-3

G-4

As for properties of the EL devices, current-voltage properties were measured with a micro-ammeter 4140B manufactured by Hewlett-Packard Co., and light emission luminance was measured with BM7 manufactured by Topcon Corp. In Examples 9 to 14, organic light-emitting devices were produced as in Example 8 except that the guest materials and the host materials were changed, and were evaluated as in Example 8. The host materials were compounds shown in Table 3 and are shown in the column, G-2, in Table 4.

The luminous efficiencies and the voltages in Examples 7 to 14 are shown in Table 4.

TABLE 4

|  | Guest | G-2 | Luminous Efficiency (cd/A) | Voltage (V) |
| --- | --- | --- | --- | --- |
| Example 7 | A2 | H8 | 13.2 | 3.5 |
| Example 8 | A5 | H16 | 13.7 | 3.4 |
| Example 9 | A5 | H21 | 13.4 | 3.4 |
| Example 10 | A7 | H15 | 13.7 | 3.8 |
| Example 11 | A11 | H7 | 13.8 | 3.5 |
| Example 12 | A17 | H21 | 13.5 | 3.6 |
| Example 13 | A25 | H23 | 12.9 | 3.5 |
| Example 14 | A33 | H9 | 13.9 | 3.5 |

Examples 15 to 19

In Example 15, an organic light-emitting device having a structure of sequentially laminated (anode)/(hole-injecting layer)/(hole-transporting layer)/(light-emitting layer)/(electron-transporting layer)/(electron-injecting layer)/(cathode) was produced.

An organic light-emitting device having a resonance structure was produced by the following method: An aluminum alloy (AlNd) film serving as a reflective anode was formed on a support of a glass substrate by sputtering so as to have a thickness of 100 nm. Then, an ITO film serving as a transparent anode was formed thereon by sputtering so as to have a thickness of 80 nm. Furthermore, a device isolation film of polyimide having a thickness of 1.5 μm was formed at the peripheral regions of the anodes, and an opening having a radius of 3 mm was formed. The resulting product was washed by ultrasonic cleaning with acetone and then isopropyl alcohol (IPA) and then washed by boiling in IPA, followed by drying. Furthermore, the surface of this substrate was washed with UV.

Furthermore, organic layers shown below were sequentially formed by vacuum deposition by resistance heating in a vacuum chamber of $10^{-5}$ Pa, and then a transparent electrode having a thickness of 30 nm was formed as a cathode by sputtering IZO. After the formation, sealing was performed in a nitrogen atmosphere.

Thus, an organic light-emitting device was formed.
hole-injecting layer (135 nm): G-11
hole transporting layer (10 nm): G-12
light-emitting layer (35 nm): compound H9 (host), example compound A2 (guest, weight ratio: 2%)
electron-transporting layer (10 nm): G-14
electrode-injecting layer (70 nm): G-15 (weight ratio: 80%), Li (weight ratio: 20%)

[Chem. 24]

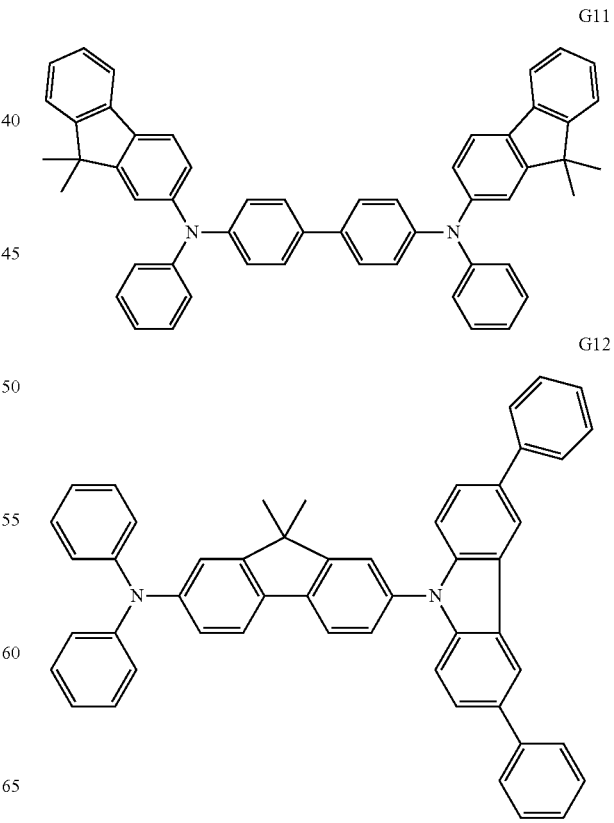

G11

G12

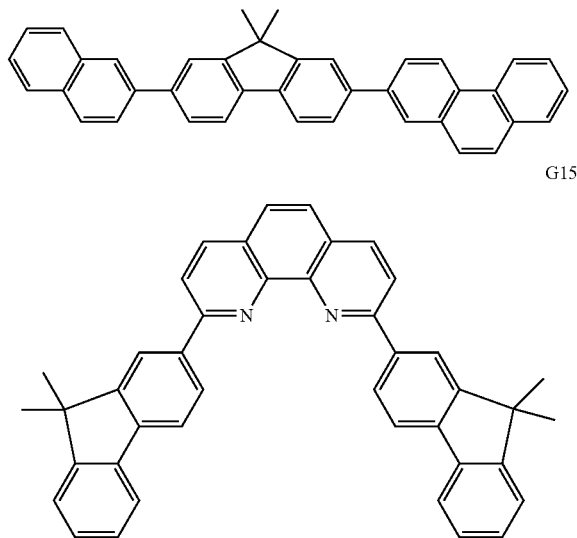

G14

G15

As for properties of the organic light-emitting device, the current-voltage properties were measured with a micro-ammeter 4140B manufactured by Hewlett-Packard Co., and the light emission luminance was measured with BM7 manufactured by Topcon Corp. In Examples 16 to 19, organic light-emitting devices were produced as in Example 15 except that the guest materials and the host materials were changed, and were evaluated as in Example 15. The host materials were compounds shown in Table 3 and are shown in the column, G-13, in Table 5.

The luminous efficiencies and the voltages of Examples 15 to 19 are shown in Table 5.

TABLE 5

|  | Guest | G-13 | Luminous Efficiency (cd/A) | Voltage (V) |
|---|---|---|---|---|
| Example 15 | A2 | H9 | 25.1 | 3.8 |
| Example 16 | A3 | H4 | 25.3 | 4.0 |
| Example 17 | A12 | H22 | 25.3 | 4.1 |
| Example 18 | A16 | H7 | 25.5 | 4.1 |
| Example 19 | A41 | H28 | 25.2 | 4.0 |

Results and Conclusion

The organic compounds according to the present invention are novel compounds having high quantum yields and being suitable for green light emission and can produce light-emitting devices exhibiting good light-emitting properties by being applied to organic light-emitting devices.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-139959, filed Jun. 18, 2010, which is hereby incorporated by reference herein in its entirety.

REFERENCE SIGNS LIST

8 TFT device
11 anode
12 organic compound layer
13 cathode

The invention claimed is:

1. An organic light-emitting device comprising a cathode, an anode, and organic compound layers disposed between the anode and the cathode, wherein
at least one layer of the organic compound layers contains the organic compound represented by the following Formula (1):

[Chem. 1]

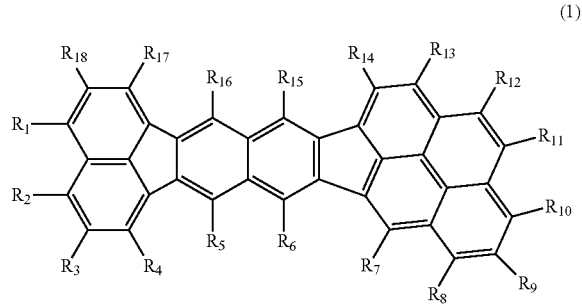

(1)

in Formula (1),
$R_1$ to $R_{18}$ are each independently selected from the group consisting of hydrogen atoms, halogen atoms, optionally substituted alkyl groups, optionally substituted alkoxy groups, substituted amino groups, optionally substituted aryl groups, and optionally substituted heterocyclic groups.

2. organic light-emitting device according to claim 1, wherein $R_1$ to $R_{18}$ are each independently selected from the group consisting of hydrogen atoms, optionally substituted alkyl groups, and optionally substituted aryl groups.

3. organic light-emitting device according to claim 1, wherein at least one of $R_5$, $R_6$, $R_{15}$, and $R_{16}$ is an optionally substituted aryl group.

4. organic light-emitting device according to claim 1, wherein the organic compound layer serves as a light-emitting layer.

5. organic light-emitting device according to claim 1, emitting green light.

6. A display apparatus comprising a plurality of pixels, wherein the plurality of pixels each include an organic light-emitting device according to claim 1 and a TFT device connected to the organic light-emitting device.

7. An image input apparatus comprising a display portion for displaying an image and an image input portion for inputting an image, wherein the display portion includes a plurality of pixels each including the organic light-emitting device according to claim 1 and a switching device connected to the organic light-emitting device.

* * * * *